US005376528A

United States Patent [19]

King et al.

[11] Patent Number: 5,376,528

[45] **Date of Patent: * Dec. 27, 1994**

[54] PROBES AND METHODS FOR THE DETECTION OF LISTERIA

[75] Inventors: Walter King, Maynard, Mass.; Jyotsna S. Shah, Nashua, N.H.; Raymond M. Nietupski, Millbury, Mass.; Susan Raposa, Cambridge, Mass.; Jane Warshaw, Newton, Mass.; Patrick Groody, Marlboro, Mass.; Jonathan Lawrie, Milford, Mass.; George Parsons, Arlington, Mass.; Donald N. Halbert; David J. Lane, both of Milford, Mass.

[73] Assignee: Amoco Corporation, Framingham, Mass.

[ * ] Notice: The portion of the term of this patent subsequent to Feb. 18, 2009 has been disclaimed.

[21] Appl. No.: 20,241

[22] Filed: Feb. 19, 1993

Related U.S. Application Data

[63] Continuation of Ser. No. 307,023, Feb. 6, 1989, abandoned.

[51] Int. Cl.$^5$ ........................ C12Q 1/68; C07H 21/04
[52] U.S. Cl. ........................................ 435/6; 536/24.32
[58] Field of Search ........................... 435/6; 536/24.32

[56] References Cited

U.S. PATENT DOCUMENTS

| | | | |
|---|---|---|---|
| 4,851,330 | 7/1989 | Kohne | 435/6 |
| 5,089,386 | 9/1987 | Stackebrandt et al. | 435/6 |

FOREIGN PATENT DOCUMENTS

| | | | |
|---|---|---|---|
| 0314294 | of 0000 | European Pat. Off. . | |
| 8705907 | 10/1987 | WIPO | 435/6 |
| 8803957 | 6/1988 | WIPO | 435/6 |

OTHER PUBLICATIONS

Rocourt et al., Intl. J. Syst. Bact. 37(3):266–270 (Jul. 1987).
Stewart et al., Nuc. Acids Res. 11 (18): 6289–6300 (1983).
Green et al., Gene 37: 261–266 (1985).
Klinger et al., *J. Assoc. Off. Anal. Chem*, 71:669–673 (1988).

*Primary Examiner*—Amelia Burgess Yarbrough
*Attorney, Agent, or Firm*—Fish & Richardson

[57] ABSTRACT

Improved nucleic acid probes capable of specifically hybridizing to rRNA of Listeria and not to rRNA of non-Listeria are described along with methods utilizing such probes for the detection of Listeria in food and other samples.

13 Claims, 3 Drawing Sheets

FIG. 1a

```
E. coli position #                  408                                     447
                                     |                                       |
Escherichia coli               5' ...GUAUGAAGAAGGCCUUCGGGUUGUAAAGUACUUUCAGCGGGG

Probe 1119                                TcCTTCCAAAAGCCTAGCATTTCATGACAACAATCTCc-5'
Probe 1212                           TcTACTTCTTCCAAAAGCCTAGCATTTCATGACAACAATCTCc-5'

Listeria monocytogenes            ...GUAUGAAGAAGGUUUUCGGAUCGUAAAGUACUGUUGUUAGAG
Listeria innocua                  ...GUAUGAAGAAGGUUUUCGGAUCGUAAAGUACUGUUGUUAGAG
Listeria seelingeri               ...GUAUGAAGAAGGUUUUCGGAUCGUAAAGUACUGUUGUUAGAG
Listeria welshimeri               ...GUAUGAAGAAGGUUUUCGGAUCGUAAAGUACUGUUGUUAGAG
Listeria ivanovii                 ...GUAUGAAGAAGGUUUUCGGAUCGUAAAGUACUGUUGUUAGAG
Listeria grayi                    ...GUGUGAAGAAGGUUUUCGGAUCGUAAAGCACUGUUGUUAGAG
Listeria murrayi                  ...GUGUGAAGAAGGUUUUCGGAUCGUAAAGCACUGUUGUUAGAG
Brochothrix thermosphacta         ...GAGCGAAGAAGGCCUUCGGGUCGUAAAGCUCUGUUGUUAGAG
Bacillus subtilis                 ...GAGUGAUGAAGGUUUUCGGAUCGUAAAGCUCUGUUGUUAGGG
Bacillus cereus                   ...GAGUGAUGAAGGCUUUCGGGUCGUAAAACUCUGUUGUCAGGG
Staphylococcus aureus             ...GAGUGAUGAAGGUCUUCGGAUCGUAAAACUCUGUUAUUAGGG
Staphylococcus epidermidis        ...GAGUGAUGAAGGUCUUCGGAUCGUAAAACUCUGUUAUUAGGG
Enterococcus faecalis             ...GAGUGAAGAAGGUUUUCGGAUCGUAAAACUCUGUUGUUAGAG
Clostridium innocuum              ...GAGUGAAGAAGGUCUUCGGAUCGUAAAGCUCUGUUGUAAGUG
Mycobacterium capricolum          ...GAGUGAUGACGGCCUUCGGGUUGUAAAGCUCUGUUGUAAGGG
Arthrobacter globiformis          ...GAGGGAUGACGGCCUUCGGGUUGUAAACCUCUUUCAGUAGGG
Streptomyces violaceroruber       ...GAGGGAUGACGGCCUUCGGGUUGUAAACCUCUUUCAGCAGGG
```

FIG. 1b

| E. coli position # (cont'd) | 448 452 456 477 484 492 |
|---|---|
| Escherichia coli | AGGAAGG-GAGUAAAGUUAAUACCUUUGCUCAUUGACGUUACCCGC |
| Probe 1152 | TTCTTGTTCCTATTCTCATTGACGAA-CAGGGAACTGCCATAGATT-5' |
| Probe 1151 | TTCTTGTTCCTATTCTCATTGACGAA-CAGGGAACTGCCAT-5' |
| Probe 1150 | TGTTCCTATTCTCATTGACGAA-CAGGGAACTGCCAT-5' |
| Probe 1120 | TGTTCCTATTCTCATTGACGAA-CAGGGAACTGC-5' |
| Core Variation | ********************** |
| Listeria monocytogenes | AAGAACAAGGAUAAGAGUAACUGCUU-GUCCCUUGACGGUAUCUAA |
| Listeria innocua | AAGAACAAGGAUAAGAGUAACUGCUU-GUCCCUUGACGGUAUCUAA |
| Listeria seeligeri | AAGAACAAGGAUAAGAGUAACUGCUG-GUCCCUUGACGGUAUCUAA |
| Listeria welshimeri | AAGAACAAGGAUAACAGUAACUGCUU-GUCCCUUGACGGUAUCUAA |
| Listeria ivanovii | AAGAACAAGGAUAAGAGUAACUGCUU-GUCCCUUGACGGUAUCUAA |
| Listeria grayi | AAGAACAAGGAUAAGAGUAACUGCUU-GUCCCUUGACGGUA... |
| Listeria murrayi | AAGAACAAGGAUAAGAGUAACUGCUU-GUCCCUUGACGGUAUCUAA |
| Brochothrix thermosphacta | AAGAACAAGGGUGAGAGUAACUGUUC-ACCCCUUGACGGUAUCUAA |
| Bacillus subtilis | AAGAACAAGUACCGUUCGAACAGGGCGGUACCUUGACGGUACCUAA |
| Bacillus cereus | AACAACAAGUGCUAGUUGAAUAAGCUGGCACCUCGACGGUACCUGA |
| Staphyloccoccus aureus | AAGGACAAAGGUGUNAGUAACUGUGC-ACAUCUUGACGGUACCUGA |
| Staphylococcus epidermidis | AAGAACAAAGGUGUAAGUAACUGUGC-ACGUCUUGACGGUACCUAA |
| Enterococcus faecalis | AAGAACAAGGACGUUAGUAACUGAAC-GUCCCnUGACGGUAUCUAA |
| Clostridium innocuum | AAGAACGGCUCAUAGAGGAAAUGCUA-UGGGAGUGACGGUAGCUUA |
| Mycobacterium capricolum | AAGAAAAAAUAGAGUAGGAAAUGACU-UUAUCUUGACAGUACCUUA |
| Arthrobacter globiformis | AAGAAGCG---------------------AAAGUGACGGUACCUGC |
| Streptomyces violaceoruber | AAGAAGCG---------------------AAAGUGACGGUACCUGC |

FIG. 1c

| | |
|---|---|
| E. coli position # (cont'd) | 493 ... 533 |
| Escherichia coli | AGAAGAAGCACCGGCUAACUCCGUGCCAGCAGCCGCGGUAAUACGG...3' |
| Probe 1118 | TcGTCTTTCGGTGCCGATTGATGCACGGTCGTCGGCGCCATTc-5' |
| Listeria monocytogenes | CCAGAAAGCCACGGCUAACUACGUGCCAGCAGCCGCGGUAAUACGU... |
| Listeria innocua | CCAGAAAGCCACGGCUAACUACGUGCCAGCAGCCGCGGUAAUACGU... |
| Listeria seeligeri | CCAGAAAGCCACGGCUAACUACGUGCCAGCAGCCGCGGUAAUACGU... |
| Listeria welshimeri | CCAGAAAGCnnCGGCUAACUACGUGCCAGCAGCnGCGGUAAUACGU... |
| Listeria murrayi | CCAGAAAGCCACGGCUAACUACGUGCCAGCAGCCCCGGUAAUACGU... |
| Brochothrix thermosphacta | CCAGAAAGCCACGGCUAACUACGUGCCAGCAGCCGCGGUAAUACGU... |
| Bacillus subtilis | CCAGAAAGCCACGGCUAACUACGUGCCAGCAGCCGCGGUAAUACGU... |
| Bacillus cereus | CCAGAAAGCCACGGCUCACUACGUGCCAGCNGCCGCGGUCAUCCGU... |
| Staphylococcus aureus | UCAGAAAGCCACGGCUAACUACGUGCCAGCAGCCGCGGUAAUACGU... |
| Staphylococcus epidermidis | UCAGAAAGCCACGGCUAACUACGUGCCAGCAGCCGCGGUAAUACGU... |
| Enterococcus faecalis | CCAGAAAGCCACGGCUAACUACGUGCCAGCAGCCGCGGUAAUACGU... |
| Clostridium innocuum | CCAGAAAGcCACGGCUAacUACGUGCCAgyAGCCGCGGUAAUacGU... |
| Mycobacterium capricolum | CCAGAAAGCCACGGCUAACUAUGUGCCAGCAGCCGCGGUAAUACAU... |
| Arthrobacter globiformis | AGAAGAAGCGCCGGCUAACUACGUGCCAGCAGCCGCGGUAAUACGU... |
| Streptomyces violaceroruber | AGAAGAAGCGCCGGCUAACUACGUGCCAGCAGCCGCGGUAAUACGU... |

PROBES AND METHODS FOR THE DETECTION OF LISTERIA

This is a continuation of application Ser. No. 307,023, filed Feb. 6, 1989, now abandoned.

FIELD OF THE INVENTION

This invention relates to detecting bacteria belonging to the genus Listeria and more specifically provides improved nucleic acid probes and compositions along with methods for their use for the specific detection of Listeria.

BACKGROUND OF THE INVENTION

The term "Listeria" as used herein, refers to the bacteria classified as such in Bergey's Manual of Systematic Bacteriology (P. H. A. Sneath (ed), 1986, 1234–1245, Williams & Wilkins). Recent 16S rRNA sequence data of *Listeria murrayi* and *Listeria grayi* together with well known phenotypic uniformities have led to a recent proposal to retain these two groups in the Listeria genus (Rocourt et al., International Journal of Systematic Bacteriology, Vol. 37, No. 3, pp 298–300 (1987)). Therefore, the term "Listeria" as used herein includes *Listeria monocytogenes, Listeria innocua, Listeria seeligeri, Listeria welshimeri, Listeria ivanovii, Listeria murrayi* and *Listeria grayi.*

Detection of Listeria is important in various medical and public health contexts. Human listeriosis has been shown to be clearly related to consumption of Listeria-contaminated foods only in the past few years. The outbreaks documenting this association (Schlech et al., New England J. Med. 308: 203–206 (1983); Fleming et al., New Eng. J. Med. 312: 404–407 (1985); U.S. Public Health Service, Centers for Disease Control, Morb. Mortal. Rpt. 34: 357–359 (1985)) have caused concern among public health officials, food manufacturers and regulatory agencies. Prior to these outbreaks, food microbiologists have been generally unaware and uninformed about this nearly ubiquitous group of organisms and the associated disease manifestations. Most efforts to improve diagnostic methods for Listeria have been based on its occurrence as a veterinary pathogen or as a cause of human neonatal infection (Hird, J. Food Protection 50: 429–433 (1987)).

Many samples cultured for Listeria (including foods) contain large, mixed microbial populations which hamper recovery and identification. Therefore, it is an aspect of the present invention to provide a novel assay system capable of rapidly detecting Listeria and which is generally applicable to environmental, food or clinical samples.

Because Listeria species other than *L. monocytogenes* have been recovered from a variety of food types, detection of such organisms in a food-processing environment may be important by virtue of their "indicator organism" status.

The presence of Listeria has been historically detected by culturing an appropriately prepared sample on microbiological media under conditions favorable for growth of these organisms (Lovett et al., J. Food Protection 50: 188–192 [1987], Anonymous, Fed. Register 53: 44148–44153 [1988]). McClain and Lee, J. Assoc. Off. Anal. Chem., 71: 660–664 [1988]). The resulting colonies are typically examined for morphological and biochemical characteristics, a process that generally is initiated 48 hours after acquisition of the sample and disadvantageously takes between 4–5 days to complete.

It is another aspect of the present invention to avoid the disadvantage associated with traditional, multi-day culturing techniques and to employ nucleic acid probes to detect Listeria.

It is yet another aspect of the present invention to provide probes which can hybridize to target regions which can be rendered accessible to the probes under normal assay conditions.

While Kohne et al., Biophysical Journal 8: 1104–1118 (1968), discuss one method for preparing probes to rRNA sequences they do not provide the teaching necessary to make Listeria specific probes.

U.S. Pat. No. 5,089,386 of Stackebrandt et al., filed Sep. 11, 1987 describes Listeria specific probes and while such probes work well, it is another aspect of the present invention to provide novel and improved Listeria probes not disclosed therein.

Pace and Campbell, Journal of Bacteriology 107: 543–547 (1971), discuss the homology of ribosomal ribonucleic acids from diverse bacterial species and a hybridization method for quantitating such homology levels. Similarly, Sogin, Sogin, and Woese, Journal of Molecular Evolution 1: 173–184 (1972), discuss the theoretical and practical aspects of using primary structural characterization of different ribosomal RNA molecules for evaluating phylogenetic relationships. Fox, Pechman, and Woese, International Journal of Systematic Bacteriology (1977), discuss the comparative cataloging of 16S ribosomal RNAs as an approach to prokaryotic systematics. These references, however, fail to relieve the deficiency of Kohne's teaching with respect to Listeria and in particular, do not provide Listeria specific probes useful in assays for detecting Listeria in food and other samples.

Ribosomes are of profound importance to all organisms because they serve as the only known means of translating genetic information into cellular proteins, the main structural and catalytic elements of life. A clear manifestation of this importance is the observation that all cells have ribosomes.

Ribosomes contain three distinct RNA molecules which, at least in *E. coli*, are referred to as 5S, 16S, and 23S rRNAs. These names historically are related to the size of the RNA molecules, as determined by their sedimentation rate. In actuality, however, ribosome molecules vary substantially in size between organisms.

Nonetheless, 5S, 16S, and 23S rRNA are commonly used as generic names for the homologous RNA molecules in any bacteria, and this convention will be continued herein.

Hybridization traditionally is understood as the process by which, under predetermined reaction conditions, two partially or completely complementary single-stranded nucleic acids are allowed to come together in an antiparallel fashion to form a double-stranded nucleic acid with specific and stable hydrogen bonds.

The stringency of a particular set of hybridization conditions is defined by the base composition of the probe/target duplex, as well as by the level and geometry of mispairing between the two nucleic acids.

Stringency may also be governed by such reaction parameters as the concentration and type of ionic species present in the hybridization solution, the types and concentrations of denaturing agents present, and/or the temperature of hybridization. Generally, as hybridization conditions become more stringent, longer probes are preferred if stable hybrids are to be formed. As a corollary, the stringency of the conditions under which a hybridization is to take place (e.g., based on the type of assay to be performed) will largely dictate the preferred probes to be employed. Such relationships are well understood and can be readily manipulated by those skilled in the art.

As a general matter, dependent upon probe length, such persons understand stringent conditions to mean approximately 35° C.–65° C. in a salt solution of approximately 0.9 molar.

As used herein, probe(s) refer to synthetic or biologically produced nucleic acids (DNA or RNA) which, by design or selection, contain specific nucleotide sequences that allow them to hybridize under defined predetermined stringencies, specifically (i.e., preferentially) to target nucleic acid sequences. Two functionally modified probes are described in the examples described herein.

Capture probes are modified in such a way that they hybridize to the target nucleic acid molecule and can be removed, along with the target molecule, from solution. Detection probes are advantageously modified by the addition of one of a variety of detectable ligands (e.g. $^{32}P$, biotin, fluorescein, etc.) which permit the direct or indirect detection of the target nucleic acid.

A target nucleic acid sequence is one to which a particular probe is capable of preferentially hybridizing.

Still other useful definitions are given as their first use arises in the following text. All references cited herein are fully incorporated by reference.

SUMMARY OF THE INVENTION

In accordance with the various principles and aspects of the present invention, there are provided improved nucleic acid probes and probe sets comprising DNA or RNA sequences which, under specific hybridization conditions, are capable of detecting the presence of ribosomal RNA (rRNA) molecules of Listeria or the DNA encoding such ribosomal molecules (rDNA), but which are not capable, under the same conditions, of detecting the rRNA or rDNA of other related bacteria which may be present in the test sample.

The present invention also features an assay system for the advantageous utilization of these probes, the format of which can enhance the aforementioned desirable behavior of the probes. Ideally, a cultivation step which enhances the growth of Listeria relative to that of other bacteria is included in the most preferred embodiment of the present assay. The microbiological selection obtained with such a cultivation step, in combination with the specificity of the described probes, has been discovered to impart enhanced performance capabilities with respect to other currently available means for detection of Listeria generally including:

a) increased sensitivity; i.e., the ability to detect Listeria in a given sample more frequently than currently available methods;

b) potentially significant reductions in assay cost due to the use of inexpensive reagents and reduced labor;

c) accurate identification of Listeria; and d) faster results because the test does not require the isolation of Listeria from the cultured samples prior to testing. Accordingly, in the most preferred embodiment of the assay, only two days are required to provide a result.

The probes of the present invention impart enhanced performance with respect to those described in U.S. Pat. No. 5,089,386 of Stackebrandt et al. in that they do not react with Brochothrix, a genus closely related to Listeria by genetic and biochemical criteria. Brochothrix is known to occur in some food and environmental samples which also support the growth of Listeria. Therefore, this characteristic of the present probe set represents a significant enhancement in performance.

It has been discovered that other advantages incurred by directing the probes of the present invention against rRNA include the fact that the rRNAs detected constitute a significant component of cellular mass. Although estimates of cellular ribosome content vary, actively growing Listeria bacteria may contain upwards of $1.0\times10E+4$ ribosomes per cell, and therefore $1.0\times10E+4$ copies of each of the rRNAs (present in a 1:1:1 stoichiometry in ribosomes). In contrast, other potential cellular target molecules such as genes or RNA transcripts thereof, are less ideal since they are present in much lower abundance.

A further unexpected advantage is that the rRNAs (and the genes encoding them) appear not to be subject to lateral transfer between contemporary organisms. Thus, the rRNA primary structure provides an organism-specific molecular target, rather than a gene-specific target as would likely be the case, for example of a plasmid-borne gene or product thereof which may be subject to lateral transmission between contemporary organisms.

Additionally, the present invention provides probes to Listeria rRNA target sequences which appear to be fully inclusive for all Listeria strains. A most preferred embodiment comprises a mixture of three probes for hybridization to the rRNA in all Listeria.

Most of the specificity of the aforementioned mixture resides in one of the probes, the capture probe. Advantageously, the rRNA target sequence of the capture probe is sufficiently different in most non-Listeria rRNAs that, under the preferred assay conditions of the present invention, the capture probe of the present invention hybridizes to Listeria rRNAs and does not hybridize with non-Listeria organisms. These probe characteristics are defined as inclusivity and exclusivity, respectively, and under the preferred assay conditions of the present invention are imparted to the aforementioned probe mixture.

The discovery that probes could be generated with the extraordinary and improved inclusivity and exclusivity characteristics of those of the present invention with respect to Listeria was unpredictable and unexpected.

In a preferred embodiment of the invention, an assay method for detecting Listeria is provided in which bacteria in the sample to be tested are preferably grown for a limited time under conditions which foster rapid and abundant growth of any Listeria in the sample and which are biased against the growth of many closely related bacteria. Hybridization analysis using the preferred probes of the present invention is then advantageously performed on the sample after this growth period.

BRIEF DESCRIPTION OF THE FIGURES AND TABLES

Further understanding of the principles and aspects of the present invention may be made by reference to the tables wherein:

FIGS. 1*a*–1*c*: Shows alignment of the nucleotide sequences of the preferred probes of the present invention with the nucleotide target sequence including the "core" region from 456 to 477 of Listeria 16S rRNA (using the *E. coli* position numbering convention) along with relevant portions of the 16S rRNAs from *Listeria monocytogenes, Listeria innocua, Listeria seeligeri, Listeria welshimeri, Listeria ivanovii, Listeria grayi, Listeria murrayi* and *Brochothrix thermosphactata, Bacillus subtilis, Bacillus cereus, Staphylococcus aureus, Streptococcus epidermidis, Enterococcus faecalis, Clostridium innocuum, Mycoplasma capricolum, Arthrobacter globiformis* and *Streptomyces violaceoruber*. RNA sequences are written 5′ to 3′, probe sequences are DNA and written 3′ to 5′. Lower case c in certain of the probes indicates a modified cytosine residue to which a reporter group may or may not be attached depending on the assay form employed.

Probes of the 1120 series (1120, 1150, 1151 and 1152) are shown, along with the "core" region of variation upon which they are based, above the "parent" sequence from *Listeria monocytogenes*. Much of the specificity of the preferred assay of the present invention resides in this series of probes, in which they are used as "capture" probes.

Probes 1118, 119 and 1212 are detection probes which are designed to be used with the 1120 series capture probes.

Table 1: Exemplifies the inclusivity behavior of the preferred probe set toward a representative sampling of Listeria strains. Inclusivity data were obtained from the preferred liquid hybridization testing format of Example 1 (General).

Table 2: Exemplifies the exclusivity behavior of the preferred probe set toward a representative sampling of non-Listeria strains. Exclusivity data were obtained from the preferred liquid hybridization testing format of Example 1 (General).

Table 3: Provides data showing detection of Listeria in food samples with the preferred probes in the preferred format of the present invention (Example 1, Specific).

DETAILED DESCRIPTION OF THE INVENTION AND BEST MODE

Probe Development Strategy

The first step taken in the development of the probes of the present invention involved identification of regions of 16S and/or 23S rRNA which potentially could serve as target sites for Listeria specific nucleic acid probes. As a practical matter, it is difficult to predict, a priori, which non-Listeria organisms might be present in any test sample.

Because of the large number of such potential non-Listeria bacteria, demonstrating exclusivity for any given probe sequence is not only unpredictable but also extremely difficult and laborious. A more rigorous criterion was adopted to obviate the need to know what non-Listeria bacteria might be present in all test samples that ultimately will be screened using the probes.

This entailed knowledge of the phylogenetic relationships among Listeria and between Listeria and other groups of bacteria.

Specifically, an operating but previously unproven hypothesis was adopted that the exclusivity criterion could be satisfied by determining that if a particular target region in Listeria rRNA could be identified which was sufficiently different from the homologous region in the rRNA of representative yet close evolutionary relatives of Listeria, then a probe to such a sequence could be used to distinguish between Listeria and the relatives by hybridization assay. Based on phylogenetic observations, it then was extrapolated that rRNA sequences of more distantly related organisms, even though their actual identity may not necessarily be known, should be predictably different in a particular region of sequence than the aforementioned close evolutionary relative of Listeria. However, it cannot be predicted, a priori whether such regions exist or if they do, where within the rRNA such regions will be located.

As the first step in identifying regions of Listeria rRNA which could potentially serve as useful target sites for nucleic acid hybridization probes, nearly complete nucleotide sequences of the 16S rRNAs from isolates representing all seven Listeria species were determined including five isolates of *L. monocytogenes* and two isolate of *L. innocua*. These were arbitrarily selected as representative of the evolutionary breadth of genus Listeria.

The nucleotide sequences of various portions of the rRNAs were determined by standard laboratory protocols either by cloning (Maniatis et al., 1982, Molecular Cloning: A Laboratory Manual, Cold Spring Harbor Laboratory, New York, pp 545) and sequencing (Maxam & Gilbert, 1977, Proceedings of the National Academy of Science, USA 74: 560–564; Sanger et al., 1977, Proceedings of the National Academy of Science, USA 74: 5463–5467) the genes which specify the rRNAs, and/or by direct sequencing of the rRNAs themselves using reverse transcriptase (Lane et al., [1985], Proceedings of the National Academy of Science, USA 82: 6955–6959).

The determined Listeria rRNA nucleotide sequences were compared to one another and to other available rRNA nucleotide sequences, in particular to those of closely related bacteria such as Brochothrix, Staphylococcus, Streptococcus, Enterococcus, and Bacillus, which also were determined as part of this work.

One region of sequence was identified which appeared to be conserved among all Listeria and which, importantly, is different in all other bacterial sequences analyzed or tested by hybridization. This preferred region of sequence is shown in FIG. 1.

Because of the extremely large number of organisms potentially relevant to defining exclusivity, and inclusivity (on the order of 7 species and biogroups of Listeria) and the inclusivity characteristics of the test probes, an iterative strategy was adopted to test and refine potential probes. The probes were conveniently synthesized by standard phosphoramidite (Caruthers, M. H. et al. [1983], in Gene Amplification and Analysis, eds. Papas, T. S., Rosenberg, M., Charikjian, J. G., Pub. Elsevier, New York, Vol. 3 pp. 1–26) techniques on an Applied Biosystems instrument.

A list of 292 Listeria isolates covering all 7 Listeria species is shown in Table 1. In the preferred assay format, the probes demonstrated excellent inclusivity characteristics—detecting all 292 isolates.

A list of non-Listeria bacteria which exemplify the type of bacteria that may be present in potentially Listeria containing samples and which are closely related to Listeria, is given in Table 2. Note that these also represent many of the genera most closely related to Listeria. In the preferred assay format, the probes demonstrated excellent exclusivity characteristics—detecting none of the tested non-Listeria isolates.

A probe which demonstrates good exclusivity characteristics to such a broad representation of bacteria can reasonably be predicted to behave similarly toward a much broader list of more distantly related organisms.

The final steps of probe design and analysis ideally comprise testing real samples (e.g., food/clinical/environmental) and then selecting suitable probes for a final probe set so that the desirable properties are optimized under realistic test conditions.

Physical Description of Probes

The foregoing probe selection strategy yielded a number of probes useful for identifying Listeria bacteria in samples. The following preferred oligonucleotide probes are disclosed herein:

Probe 1118: 5′-cTTACCGCGGCTGCTGGCACGTAGTTAGCCGTGGCTTTCTGcT-3′

Probe 1212: 5′-cCTCTAACAACAGTACTTTACGATCCGAAAACCTTCTTCATcT-3′

Probe 1120: 5′-CGTCAAGGGACAAGCAGTTACTCTTATCCTTGT-3′

FIGS. 1*a–c* shows these probe sequences (and a number of derivatives thereof) aligned upon their target sequences in the 16S rRNAs of representative Listeria strains. Three groups of probes, corresponding to probes 1118, 1212 and 1120, above, are shown in FIGS. 1*a–c*.

Probes of the 1120 group (probes 1120, 1150, 1151 and 1152) are targeted at the region of 16S rRNA sequence corresponding approximately to nucleotide positions 448 to 492 (using the *E. coli* numbering convention). These probes make use of the region of sequence variability which was discovered to be the most useful for differentiating Listeria from other bacteria, and which is indicated as the region of "core variation" in FIGS. 1*a–c*. In the preferred assay format of the present invention (see Example 1) these probes are used to "capture" the target Listeria 16S rRNA molecules in the sample and to remove them from the lysed sample solution. For this purpose, they will have between 20 and 200 deoxyadenosine (dA) residues (not shown in FIG. 1) appended to their 3′ termini to serve as "handles" for removing the target/probe complex from the sample solution. Under the hybridization stringencies employed in Example 1, probe 1120 is of optimal length and geometry (with respect to the core region of variation) for obtaining the desirable inclusivity and exclusivity behavior characteristics recorded in those experiments. Probes 1150, 1151 and 1152 are longer "versions" of probe 1120 which would be more useful under higher stringency hybridization conditions. Similarly, shorter versions of the 1120 probe, centered around the core region of variation, would be more useful under lower stringency hybridization conditions (e.g., such as those that could be applied in a dot blot format).

The probe group comprised of probes 1212 and 1119 and the "group" represented by probe 1118 are designed as detection probes (according to the previously given definition) and are designed to be used in conjunction with the 1120 series capture probes described above.

Probes 1119 and 1212 are simply length variants of one another. Both are targeted at essentially the same region of Listeria 16S rRNA, spanning nucleotide positions ca. 408 to 447 (using the *E. coli* numbering convention). In the illustration of the preferred assay format given in Example 1, probe 1119 was utilized. Subsequently, probe 1212 was designed to more closely match the hybridization characteristics of probe 1120 and probe 1118 with which it is simultaneously used. For purposes of this invention, probes 1119 and 1212 are deemed variations of one another and essentially equivalent in hybridization behavior.

The salient features of either probe 1119 and 1212 are: 1) the proximity of their target site to that of probe 1120, and 2) the sequence differences between their target site in Listeria and non-Listeria 16S rRNAs. Although not as strongly different between Listeria and the very closely related Brochothrix as the probe 1120 target sequence, the probe 1119/1212 target sequence nevertheless is variable enough to lend some additional specificity to the probe 1120-containing set. Moreover, the 1119/1212 target sequences diverge to progressively greater extents as one inspects sequences from bacteria more distant from Listeria than Brochothrix (e.g., Bacillus, Staphylococcus, Streptococcus, etc.). The proximity of the probe 1119/1212 target sequence to the target sequence of probe 1120 is important for a number of reasons, including the lessening or abolition of the potential for degradation of the target rRNA by endogenous ribonucleases in the sample. Such degradation would tend to "unlink" the capture and detection probes in the preferred assay format (although other specific features of the preferred assay format also ameliorate this effect) and thereby lessen the observed assay signal. The proximity of the probe 1119/1212 target sequence to the probe 1120 target region also serves to improving the "accessibility" of the probe 1120 target site for hybridization by that probe by disrupting nearby intramolecular structure of the target RNA itself. This tends to generate high overall positive signal levels in the assay.

Like probes 1119 and 1212, probe 1118 also is designed as a detection probe and its target site also flanks the target probe 1120 target site. Probe 1118 adds little if any specificity to the preferred probe set because there is virtually no sequence variation through its target region among the Gram positive bacteria show in FIGS. 1*a–c*. Indeed, this region of sequence is nearly constant in all 16S (and eukaryotic 18S) rRNA so far inspected. The intended functions of probe 1118 are: 1) to promote maximum accessibility of the probe 1120 target site by disrupting native secondary structure in the vicinity of the probe 1120 target site, and 2) to provide incorporation of additional detection ligand into the captured target/probe complex over and above what can be provided by hybridization of only the 1212 (or 1119) detection probes.

The sequence data in FIG. 1 suggest that probes 1118, 1119 and 1120 should hybridize quite widely among Listeria. The five strains of *L. monocytogenes* (all natural isolates from a variety of food sources) whose 16S rRNAs were inspected in detail all have identical sequences through these target regions (indicated simply as *Listeria monocytogenes* in FIG. 1). Likewise, the 16S rRNAs of *L. innocua* (2 strains), *L. seeligeri, L. welshimeri, L. ivanovii, L. grayi* and *L. murrayi* all conform to the *L. monocytogenes* sequence through these target regions. Some minor variations exist, for example *L. grayi* and *L. murrayi* 16S rRNAs also are virtually identical in sequence through these regions with only one position showing minor variation in the probe 1212/1119 target site (FIG. 1, position 434). Nevertheless, this is a small collection of Listeria 16S rRNA sequences compared to the number of known isolates.

Our experience with other rRNA-targeted Listeria probes (Stackebrandt et al., copending U.S. Ser. No. 096,570) and rRNA-targeted probes for species of other genera (e.g. Salmonella, U.S. Ser. No. 277,579; Yersinia, U.S. Ser. No. 169,646; and *E. coli*, U.S. Ser. No. 233,683) have taught us quite clearly that the comparative sequence data can be nothing more than an encouraging first indication that a useful probe might exist. Potentially, much greater sequence variation might exist in other Listeria strains not inspected by sequence analysis. Such variation might reduce or eliminate hybridization by the prospective probes to some or many untested Listeria strains. Therefore, carefully documenting the hybridization behavior of the probes to a large number of Listeria isolates is an important element in documenting that such probes are capable of detecting all Listeria or, failing that, for documenting which Listeria are not detected. Such hybridization experiments are described below, the data for which are provided in Table 1. Some 292 Listeria strains, isolated from a wide variety of sources, were tested for reactivity toward the preferred probe set (Example 1), all were strongly positive. This was not a predictable result, even with the fairly extensive 16S rRNA sequence data described above.

Equally as important as the inclusivity behavior of the probes, is their exclusivity, i.e., their reactivity toward non-Listeria bacteria. Particularly important in this regard is their reactivity toward non-Listeria which might also be present in the same environments as Listeria. Results of such exclusivity testing are provided in Table 2. All non-Listeria strains tested (some 27 non-Listeria genera are represented) were negative, i.e. generated absorbancies in the preferred colorometric assay format of less than 0.1 Absorbance units.

In interpreting these results, it must be borne in the mind that inclusivity and exclusivity behavior are highly interdependent characteristics. To a reasonable approximation both inclusivity and exclusivity behavior of a probe will be a function of: 1) the range of sequence variation found in the probe target regions in target and non-target organisms; 2) the physical characteristics of the probe; and 3) the stringency of hybridization employed. Given any particular target region, one has no experimental control over (1), this is given in nature. As discussed above, (2) and (3) are highly dependent upon one another and, in practice are "adjusted" in parallel. However, in considering any particular probe, one is left only with (3) being available for experimental manipulation. In considering the exclusivity behavior of a particular probe (or probe set) it is therefore important to recognize that inclusivity and exclusivity behavior of a specific probe (or probe set) must be documented under identical or equivalent hybridization conditions.

To understand this interrelationship, consider the following hypothetical example of probe/assay development. A promising target region is discovered by comparative sequence analysis as discussed above. A test probe is designed which will hybridize to this region. Upon testing under hybridization stringency 1 (HS1), it hybridizes readily to all target organisms (Listeria) tested (an oversimplification). Upon testing of non-target organisms under (HS1) conditions, some undesirable cross-hybridization of the probe(s) is discovered. To lessen or, more preferably, eliminate this undesirable cross-hybridization, stringency must be increased—e.g. by shortening the probe, raising the temperature or lowering the salt concentration of the hybridization and/or wash solution. One can systematically or randomly try any number of combinations of any or all these measures progressively increasing the stringency until the offending cross-hybridization is reduced to "acceptable" levels. Call this hybridization stringency 2 (HS2). In practice, there is a very real limit on how far stringency of hybridization can be increased. That is, one can only increase stringency to a point where hybridization signal to the target organisms themselves decreases to an "unacceptable" level. Such experimental manipulations and limitations are well understood by those skilled in the art of nucleic acid hybridization.

If the target region in the offending non-target organism is identical to that occurring in one or more of the target organisms then, predictably, no differentiation of target and non-target organisms is possible with any probes to that target region under any hybridization conditions. This can be determined unambiguously by sequencing the target region of the offending organism.

If the target region in the offending non-target organism is not identical to that occurring in the target organisms, but only closely related, then it cannot be predicted whether one will be able to discover acceptable stringency conditions (i.e. a given probe or probe set, and a specific set of hybridization conditions) that discriminate target from non-target organisms. In this regard, it shall be noted that the inclusivity data shown in Table 1 and the exclusivity data shown in Table 2 were generated with the same probe set (capture probe 1120, detection probes 1118 and 1119) under identical assay conditions. Therefore, under conditions where the assay detects 100% of the Listeria strains tested, it was unexpectedly discovered not to cross-hybridize to any of the tested non-Listeria bacteria.

Hybridization Analyses of Probe Behavior

Hybridization behavior of the probes toward representative Listeria and non-Listeria was determined in two basic ways. The first method was the testing under actual assay conditions of pure cultures of numerous Listeria and non-Listeria strains. These data are provided in Tables 1 and 2. This pure culture testing was augmented by hybridization assays performed on cultures of uninoculated and Listeria-containing food and environmental samples. These food and environmental tests ensured that Listeria could be detected under actual "field" conditions in which such a test would be most valuable. They also served to significantly expand the exclusivity testing in a highly relevant manner because cultures from uninoculated samples generally provided high levels of varied non-Listeria bacteria that often are present and selectively enriched in such test samples. To duplicate this range of exclusivity testing using pure cultures of such non-Listeria isolates would be more tedious and potentially irrelevant because the selective enrichment does not necessarily select those non-Listeria organisms most closely related to Listeria. Instead, optimal growth conditions and resistance to antibiotics are the major determinants of isolates which will be present following enrichment. Only a small, representative sampling of the food testing data is shown in Table 3. Overall, some 1500 samples have so far been tested and fully bear out the results indicated in Table 3.

The preferred assay format is described below in Example 1. Example 1 1—General, describes the basic assay, including examples of the range of possible variation for some assay steps, which was used to generate the pure culture, liquid hybridization, inclusivity and exclusivity data shown in Tables 1 and 2. Some of the explicit details of the assay procedure are as given in Example 1—Specific, which details, in addition, explicit procedures used to inoculate food samples and procedures used for cultivation/enrichment of Listeria from such samples. These data are provided in Table 3.

Example 1 General and Example 1 Specific are descriptions of the same basic assay except in the level of detail provided and in the initial handling of pure culture versus food or environmental samples. All data in Tables 1, 2 and 3 were generated using the probe set 1120 (capture probe), 1118 and 1119 (detection probes) and the same hybridization regents and conditions.

Example 1—General

A Homopolymer Capture, Dual Probe, Liquid Hybridization Format

Cultures containing Listeria were grown in modified Listeria enrichment broth (Klinger et al., J. Assoc. Off. Anal. Chem. 71:669-673 [1988]) appropriate for generating selective growth of Listeria. Non-Listeria were grown in non-selective broth, either Tryptic Soy Broth with yeast extract (TSB/Ye, DIFCO) or Brain Heart Infusion Broth (BHI, DIFCO). The nucleic acids then were released by any of a number of appropriate lysis agents (e.g., NaOH, Guanidine salts, detergent, enzymatic treatment, or some combination of the aforementioned). In this example, cells were lysed upon sequential addition of three solution agents: 1) a premixed solution of lysozyme and mutanolysin, 2) proteinase K, and 3) guanidine thiocyanate.

Hybridization was carried out with a set of three probes at least one of which, but not necessarily all three, must be specific for the organism to be detected. In this example, the Listeria specific "capture" probe, probe 1120 was enzymatically tailed with ca. 200 deoxyadenosine (dA) residues at its 3' terminus (20-200 dA residues may be used with varying efficiency under different assay conditions). The reporter probes, 1118 and 1119, could be labeled either chemically or enzymatically with radioactive Phosphorous (P-32) or other small ligand (e.g., fluorescein or biotin) and used to detect the captured target molecules. In this example, the detection probes were labeled with fluorescein—which was appended chemically to the analog C residues indicated in FIG. 1.

Generally, following cultivation/enrichment of bacteria present in the test samples, small aliquots of the cultures were transferred to test tubes. The bacteria were lysed, the capture and detection probes (diluted in the chemical lysing agent, guanidine thiocyanate) were added. The solution containing the target/probe complex then was brought into contact with a surface containing bound deoxythymidine (dT) homopolymer 1500-4000 nucleotides in length, under conditions that allowed hybridization between the dA and dT. The hybridization reaction was allowed to proceed for an appropriate period of time (see below, Example 1—Specific). In this example, the dT was bound to a plastic "dipstick" which was submerged in the target/probe solution. If Listeria ribosomal RNA was present in the test sample, the dA-tailed, Listeria-specific capture probe (probe 1120) would have hybridized to the target rRNA sequences present and the probe/target complex, in turn, would be captured onto the dipstick. Unhybridized nucleic acids and cellular debris were washed away, leaving the captured DNA-RNA complex attached to the surface via the dA-dT duplex. The reporter probes also were bound to the dipstick via the chain of interactions—Capture surface-dT:dA-Capture probe:Target:Reporter Probe—only if the correct target nucleic acid was present.

The bound, ligand-derivatized (i.e., fluoresceinated, in this example) reporter probe then was detected by the addition of the ligand-binding:enzyme complex, anti-fluorescein antibody:horse radish peroxidase, although other alternatives such as streptavidin:alkaline phosphatase, etc. may be employed with appropriately derivatized detection probe.

Following incubation under conditions permitting specific formation of the detection complex, washing to remove non-bound enzyme, addition of chromogenic substrate and subsequent color development (typically 20-30 minutes), and the addition of color-termination solution, the developed color was measured spectrophotometrically.

This reading was compared to the negative control levels, a threshold or cutoff value was established, and a determination of the "significance" of the experimental levels was made. Tables 1 and 2 show the results of one such experiment, using pure cultures of various Listeria (Table 1) and non-Listeria (Table 2) bacteria. Overnight cultures of Listeria were diluted 1:100 in Modified Listeria Enrichment Broth immediately prior to the assay. This dilution generally results in a titer of between $1\times10^6$-$1\times10^7$ colony forming units per milliliter (CFU/ml). All the tested strains were detected with the vast majority of signals falling between 1.0-2.0 O.D. 450 units.

As can be seen in Table 2, all non-Listeria tested routinely yield O.D. 450 values of less than 0.1. Thus a positive assay signal is a highly significant indication of the presence of Listeria.

Example 1—Specifics

Detection of Listeria inoculated into food samples.

Some 20 food types have been tested using the preferred probe sets and the preferred assay described herein. Representative experiments with eight food types are presented in Table 3. These food types were selected because they represent a variety of product types that are routinely tested for the presence of Listeria. Uninoculated control samples as well as low and high inocula of four Listeria isolates were tested as follows.

For all food samples, culture enrichment was done by a modification of the FDA reference method (Lovett, J., FDA. Bacteriological Analytical Manual, Suppl.: 529.01-529.12 [9/87]). Twenty-five grams of the food sample was inoculated into 225 ml of phosphate buffered saline (PBS=$Na_2HPO_4$ 1.2 g, $NaH_2PO_4$ 0.22 g, NaCl 8.5 g, in a final volume of 1.0 liter of distilled water) and homogenized using a blender or Stomacher. Ten ml of the homogenate was transferred to 225 ml of Modified Enrichment Broth (MEB=Trypticase soy broth 30 g, Yeast extract 6.0 g, 3-[N-Morpholino] propanesulfonic acid—free acid [MOPS-free acid] 8.5 g, 3-[N-Morpholino] propanesulfonic acid—Na salt [MOPS-Na salt] 13.7 g, Acriflavin 15 mg, Nalidixic acid [Na salt] 40 mg, Cycloheximide, 50 mg, in a final volume of 1.0 liter of distilled water) and then incubated in a bottle for 22-26 hours at 35° C.

Secondary enrichment for cultured food samples then was performed. The primary enrichment culture was removed from incubation and mixed well. One ml of the primary enrichment culture was transferred to a bottle containing 100 ml of MEB and incubated for 22–26 hours at 35° C.

For the assay, 0.3 ml of the cultured cells was treated with 0.1 ml of an enzyme solution (150 mg Lysozyme and 3000 units of Mutanolysin in 10 ml of 0.1M Tris.HCl, 0.01M EDTA, pH 7.4) and incubated at 37° C. for 15 minutes, after which 0.1 ml of a lysis solution (50 mg of Proteinase-K in 10 ml of 0.10M Tris-Buffer, 0.005M EDTA and 5% Sarkosine pH=7.5) was added and the incubation was continued at 37° C. for an additional 15 minutes. Lysis was complete upon the addition of 0.5 ml of a 65° C. solution containing 5.0M GuSCN, 0.4M Tris-HCl pH 7.5, 0.08M EDTA and 0.2 mg/ml of dA-tailed 1120 capture probe and 0.3 mg/ml each of the fluorescein labeled detector probes 1118 and 1119.

A set of capture dipsticks was placed into the test tubes containing the bacterial lysates and the specific probe set. The tubes were incubated in a 37° C. water bath for 60 minutes to enable hybridization of specific capture and reporter probes to target nucleic acids and the capture of these specific DNA/rRNA hybrids to the dipsticks.

After hybridization, the dipsticks were washed by dipping them in a wash basin containing enough wash solution to cover the active part of the dipstick (50 mM Tris, pH 7.5, 150 mM NaCl, 2 mM EDTA, and 0.1% Tween 20) for 1 minute at room temperature. This process was then immediately repeated in fresh solution at 65° C. for one minute. The dipsticks containing the captured target complex were blotted onto absorbant paper and placed in tubes containing 0.75 ml antibody-enzyme conjugates (anti-fluorescein-horse radish peroxidase diluted in wash buffer), and allowed to incubate at room temperature for 20 minutes.

After allowing the antigen-antibody reaction to occur, the dipsticks were removed from the test tubes, washed twice in wash buffer at room temperature, blotted and placed into a set of labelled test tubes containing 0.75 ml of substrate-chromogen mixture (2:1 tetramethylbenzidine: hydrogen peroxide, v/v) and allowed to incubate at room temperature for 30 minutes. The dipsticks then were removed and the color development step terminated by the addition of 0.25 ml 4N sulfuric acid. The optical density (O.D.) of the samples was measured spectrophotometrically at 450 nm.

These experimental O.D. values were compared to that obtained using a non-Listeria, negative control bacterium. In these experiments, *Streptococcus faecium* was used as a negative control because in earlier, lower-stringency hybridization experiments it was the most difficult to distinguish, non-Listeria bacterium found. *S. faecium* therefore served as a rigorous control for the proper functioning of assay components and proper technical execution of the assay. Under the assay conditions described above, *S. faecium* produced spectrophotometric signals of less than 0.1 O.D. units.

As can be seen in Table 3, there were 51 samples from which Listeria was isolated from either primary or secondary enrichment broths on selective LPM agar (Lee, W. H., and McClain D., Appl. Environ. Microbiol. 52: 1215–1217 [1986]) and also detected by the non-isotopic hybridization assay of the present invention after 48 hour of cultivation.

Use of End-Capped Oligonucleotides

A further embodiment of this invention incorporates the use of end-capped oligonucleotides. These end-capped probes differ from the uncapped oligonucleotide sequences in that the capped probes contain chemical moieties which are incorporated for the purpose of blocking the 3′ and/or 5′ terminal hydroxyl groups of the oligonucleotide chain. These blocking groups impart unique stability properties to the probe because they are no longer susceptible to degradation by a variety of exonucleases which are known to degrade oligonucleotide sequences.

The preparation of the blocked probes can be accomplished using modifications of standard, published methods which are used to synthesize oligonucleotides (S. L. Beaucage and M. H. Caruthers (1981), Tetrahedron Letters 22, 1859–1862; S. Agrawal, C. Christodoulou and M. Gait (1986), Nucleic Acids Research 14, 6227–6245; J. M. Coull, H. L. Weith and R. Bischoff (1986), Tetrahedron Letters 27, 3991–3994).

These modifications incorporate the use of any of a variety of non-nucleoside phosphoramidites which can be attached to the 3′ and/or 5′ hydroxyl groups of synthetic DNA chains. Since these reagents effectively block one or both of the terminal hydroxyl groups, the resulting synthetic oligonucleotide is resistant to exonuclease digestion.

Examples of reagents which can be used in this application include but are not limited to the 5′ Amino-modifiers which are available from companies such as Glen Research Corporation (Herndon, Va.) or Clontech (Palo Alto, Calif.). Blocking of the oligonucleotides is accomplished by adding the non-nucleoside phosphoramidite to the appropriate end or ends of the synthetic oligonucleotide. Generally, the Amino-modifier is dissolved in dry acetonitrile or dichloromethane to a final concentration of 0.1M. The resulting solution is then placed onto an appropriate port of an automated DNA synthesizer. All of the necessary operations such as coupling, oxidizing and deblocking of the blocking reagent are conducted as described in instrument operations manuals such as those which are provided by Applied Biosystems (Foster City, Calif.) or Biosearch (San Rafel, Calif).

While the description of the invention has been made with reference to detecting rRNA, it will be readily understood that the probes described herein and probes complementary to those described herein will also be useful to detect the genes (DNA) encoding the rRNA (i.e., rDNA) and accordingly, such probes are to be deemed equivalents to the described probes and encompassed within the spirit and scope of the present invention and the appended claims.

TABLE 1

LISTERIA INCLUSIVITY STUDY

| ORGANISM | SOURCE | I.D. NUMBER | SERO TYPE | O.D. 450 nm | HYB+ |
|---|---|---|---|---|---|
| *L. GRAYI* | 7 | CIP6818 | | 1.30 | 1 |
| *L. GRAYI* | 8 | 2159 | | 1.56 | 1 |
| *L. INNOCUA* | 7 | CIP8011 | | 1.49 | 1 |
| *L. INNOCUA* | 10 | 16-21B-1250 | | 1.96 | 1 |
| *L. INNOCUA* | 1 | 33090 | 6A | 1.56 | 1 |

TABLE 1-continued

| LISTERIA INCLUSIVITY STUDY | | | | | |
|---|---|---|---|---|---|
| ORGANISM | SOURCE | I.D. NUMBER | SERO TYPE | O.D. 450 nm | HYB+ |
| *L. INNOCUA* | 8 | 6719 | 6A | 2.08 | 1 |
| *L. INNOCUA* | 8 | 6702 | 6A | 2.15 | 1 |
| *L. INNOCUA* | 8 | 6743 | 6B | 1.86 | 1 |
| *L. INNOCUA* | 8 | 6766 | 6B | 1.69 | 1 |
| *L. INNOCUA* | 8 | 6752 | 6B | 2.26 | 1 |
| *L. INNOCUA* | 8 | 6749 | 6B | 0.26 | 1 |
| *L. INNOCUA* | 8 | 6738 | 8B | 1.10 | 1 |
| *L. INNOCUA* | 8 | 6765 | 4B | 2.27 | 1 |
| *L. INNOCUA* | 8 | 6920 | 8A | 2.08 | 1 |
| *L. INNOCUA* | 8 | 5541 | 6A | 2.01 | 1 |
| *L. INNOCUA* | 8 | 6579 | 6B | 0.82 | 1 |
| *L. INNOCUA* | 8 | 6490 | 6B | 2.08 | 1 |
| *L. INNOCUA* | a | 6880 | 6B | 1.54 | 1 |
| *L. INNOCUA* | 8 | 6975 | 6B | 1.72 | 1 |
| *L. INNOCUA* | 8 | 6159 | 6A | 2.07 | 1 |
| *L. INNOCUA* | 8 | 6881 | 6B | 2.37 | 1 |
| *L. INNOCUA* | 8 | 7026 | 6B | 1.62 | 1 |
| *L. INNOCUA* | 8 | 7027 | 6B | 1.40 | 1 |
| *L. INNOCUA* | 8 | 7113 | 6B | 0.76 | 1 |
| *L. INNOCUA* | 8 | 7029 | 6B | 1.96 | 1 |
| *L. INNOCUA* | 8 | 7116 | 6A | 0.84 | 1 |
| *L. INNOCUA* | 8 | 7028 | 6B | 1.43 | 1 |
| *L. INNOCUA* | 8 | 7136 | 6A | 2.26 | 1 |
| *L. INNOCUA* | 8 | 7112 | 6B | 0.63 | 1 |
| *L. INNOCUA* | 3 | RM168 | | 1.73 | 1 |
| *L. INNOCUA* | 3 | RM266 | | 1.36 | 1 |
| *L. INNOCUA* | 3 | RM347 | | 1.71 | 1 |
| *L. INNOCUA* | 3 | RM371 | | 2.10 | 1 |
| *L. INNOCUA* | 3 | RM416 | | 1.89 | 1 |
| *L. INNOCUA* | 2 | F8595 | | 1.68 | 1 |
| *L. INNOCUA* | 2 | F8615 | 6A | 2.22 | 1 |
| *L. INNOCUA* | 2 | F2396 | | 2.12 | 1 |
| *L. INNOCUA* | 2 | F8595 | | 2.11 | 1 |
| *L. INNOCUA* | 1, 2 | 33090, KC1783 | | 2.16 | 1 |
| *L. INNOCUA* | 4 | LA-1 | | 2.20 | 1 |
| *L. IVANOVII* | 7 | CIP7843 | | 1.59 | 1 |
| *L. IVANOVII* | 8 | 5756 | 5 | 2.26 | 1 |
| *L. IVANOVII* | 8 | 6032 | 6 | 1.88 | 1 |
| *L. IVANOVII* | 8 | 5755 | 5 | 1.61 | 1 |
| *L. IVANOVII* | a | 6736 | 5 | 2.10 | 1 |
| *L. IVANOVII* | 8 | 3769 | 5 | 2.20 | 1 |
| *L. IVANOVII* | 8 | 3889 | 5 | 1.70 | 1 |
| *L. IVANOVII* | 8 | 5378 | 5 | 1.62 | 1 |
| *L. IVANOVII* | 8 | 5380 | 5 | 1.86 | 1 |
| *L. IVANOVII* | 1, 2 | 19119, KC1786 | | 2.27 | 1 |
| *L. IVANOVII* | 2 | F6984 | | 2.15 | 1 |
| *L. IVANOVII* | 4 | LA29 | | 2.29 | 1 |
| *L. MONOCYTOGENES* | 5 | 3168 | | 1.49 | 1 |
| *L. MONOCYTOGENES* | 1 | 15313 | | 1.42 | 1 |
| *L. MONOCYTOGENES* | 4 | 000169 | | 1.49 | 1 |
| *L. MONOCYTOGENES* | 5 | 3177 | | 1.15 | 1 |
| *L. MONOCYTOGENES* | 8 | Culture A | | 0.86 | 1 |
| *L. MONOCYTOGENES* | 8 | Culture B | | 2.09 | 1 |
| *L. MONOCYTOGENES* | 8 | Culture C | | 1.15 | 1 |
| *L. MONOCYTOGENES* | 10 | 17D-185-354 | | 0.91 | 1 |
| *L. MONOCYTOGENES* | 10 | 141-130-131 | | 1.57 | 1 |
| *L. MONOCYTOGENES* | 2 | 15-438-143 | | 1.16 | 1 |
| *L. MONOCYTOGENES* | 2 | 20-C83-P286 | | 1.63 | 1 |
| *L. MONOCYTOGENES* | 2 | 19C-84-6807 | | 1.77 | 1 |
| *L. MONOCYTOGENES* | 7 | CIP2754 | | 2.08 | 1 |
| *L. MONOCYTOGENES* | 7 | CIP1929 | | 1.93 | 1 |
| *L. MONOCYTOGENES* | 7 | CIP2750 | | 2.27 | 1 |
| *L. MONOCYTOGENES* | 7 | CIP1890 | | 2.17 | 1 |
| *L. MONOCYTOGENES* | 7 | CIP1826 | | 1.95 | 1 |
| *L. MONOCYTOGENES* | 7 | CIP1826 | | 0.56 | 1 |
| *L. MONOCYTOGENES* | 7 | CIP1817 | | 2.01 | 1 |
| *L. MONOCYTOGENE* | 7 | CIP1820 | | 1.13 | 1 |
| *L. MONOCYTOGENES* | 7 | CIP1820 | | 2.05 | 1 |
| *L. MONOCYTOGENES* | 7 | 9644 | | 1.68 | 1 |
| *L. MONOCYTOGENES* | 1 | 19111 | 1 | 2.14 | 1 |
| *L. MONOCYTOGENES* | 1 | 19115 | 4B | 1.39 | 1 |
| *L. MONOCYTOGENES* | 11 | H-1 | | 1.92 | 1 |
| *L. MONOCYTOGENES* | 11 | TYPE 1 | 1 | 2.16 | 1 |
| *L. MONOCYTOGENES* | 11 | 4131 | | 2.27 | 1 |
| *L. MONOCYTOGENES* | 11 | TYPE-4 | 4 | 1.82 | 1 |
| *L. MONOCYTOGENES* | 11 | B64131 | | 2.25 | 1 |
| *L. MONOCYTOGENES* | 2 | F8417 | | 1.07 | 1 |
| *L. MONOCYTOGENES* | 2 | F8833 | 1/2B | 1.30 | 1 |
| *L. MONOCYTOGENES* | 2 | F8935 | 1/2A | 2.11 | 1 |

TABLE 1-continued

LISTERIA INCLUSIVITY STUDY

| ORGANISM | SOURCE | I.D. NUMBER | SERO TYPE | O.D. 450 nm | HYB+ |
|---|---|---|---|---|---|
| *L. MONOCYTOGENES* | 2 | F8921 | 4B | 2.25 | 1 |
| *L. MONOCYTOGENES* | 2 | F7142 | 4B | 1.55 | 1 |
| *L. MONOCYTOGENES* | 2 | 7010 | 4B | 1.25 | 1 |
| *L. MONOCYTOGENES* | 2 | F8418 | 4 | 2.28 | 1 |
| *L. MONOCYTOGENES* | 8 | 6671 | 4B | 1.51 | 1 |
| *L. MONOCYTOGENES* | 8 | 5807 | 3A | 1.43 | 1 |
| *L. MONOCYTOGENES* | 8 | 6736 | 1/2B | 2.27 | 1 |
| *L. MONOCYTOGENES* | 8 | 6655 | 4B | 1.91 | 1 |
| *L. MONOCYTOGENES* | 8 | 3559 | 1/2A | 2.05 | 1 |
| *L. MONOCYTOGENES* | 8 | 6970 | 1/2A | 2.11 | 1 |
| *L. MONOCYTOGENES* | 8 | 6887 | 4B | 1.75 | 1 |
| *L. MONOCYTOGENES* | 8 | 6190 | 1/2A | 1.12 | 1 |
| *L. MONOCYTOGENES* | 8 | 5877 | 1/2B | 2.17 | 1 |
| *L. MONOCYTOGENES* | 8 | 6465 | 4B | 1.08 | 1 |
| *L. MONOCYTOGENES* | 8 | 6773 | 1/2A | 1.72 | 1 |
| *L. MONOCYTOGENES* | 8 | 6723 | 1/2B | 2.07 | 1 |
| *L. MONOCYTOGENES* | 8 | 6797 | 1/2C | 2.13 | 1 |
| *L. MONOCYTOGENES* | 8 | 6768 | 1/2C | 0.40 | 1 |
| *L. MONOCYTOGENES* | 8 | 6929 | 1/2B | 2.25 | 1 |
| *L. MONOCYTOGENES* | 8 | 6763 | 4B | 2.00 | 1 |
| *L. MONOCYTOGENES* | 8 | 6483 | 6B | 2.14 | 1 |
| *L. MONOCYTOGENES* | 8 | 6721 | 1/2C | 2.16 | 1 |
| *L. MONOCYTOGENES* | 8 | 6458 | 4B | 2.14 | 1 |
| *L. MONOCYTOGENES* | 8 | 6787 | 1/2B | 2.26 | 1 |
| *L. MONOCYTOGENES* | 8 | 6518 | 1/2C | 1.95 | 1 |
| *L. MONOCYTOGENES* | 8 | 6192 | 3B | 2.12 | 1 |
| *L. MONOCYTOGENES* | 8 | 6876 | 1/2A | 1.10 | 1 |
| *L. MONOCYTOGENES* | 8 | 6762 | 1/2A | 1.90 | 1 |
| *L. MONOCYTOGENES* | 8 | 6866 | 1/2A | 2.28 | 1 |
| *L. MONOCYTOGENES* | 8 | 6697 | 1/2A | 2.27 | 1 |
| *L. MONOCYTOGENES* | 8 | 6537 | 1/2A | 1.83 | 1 |
| *L. MONOCYTOGENES* | 8 | 6158 | 3B | 1.01 | 1 |
| *L. MONOCYTOGENES* | 8 | 6963 | 4B | 1.86 | 1 |
| *L. MONOCYTOGENES* | 8 | 6579 | 6B | 1.81 | 1 |
| *L. MONOCYTOGENES* | 8 | 6193 | 3B | 1.28 | 1 |
| *L. MONOCYTOGENES* | 8 | 6933 | 1/2C | 1.90 | 1 |
| *L. MONOCYTOGENES* | 8 | 5802 | 3A | 2.09 | 1 |
| *L. MONOCYTOGENES* | 8 | 6753 | 3C | 2.09 | 1 |
| *L. MONOCYTOGENES* | 8 | 6863 | 1/2A | 2.26 | 1 |
| *L. MONOCYTOGENES* | 8 | 6560 | 3B | 2.00 | 1 |
| *L. MONOCYTOGENES* | 8 | 6869 | 1/2C | 1.90 | 1 |
| *L. MONOCYTOGENES* | 8 | 6999 | 4A | 0.83 | 1 |
| *L. MONOCYTOGENES* | 8 | 6848 | 3C | 1.90 | 1 |
| *L. MONOCYTOGENES* | 8 | 6842 | 4B | 1.26 | 1 |
| *L. MONOCYTOGENES* | 8 | 6845 | 3B | 2.14 | 1 |
| *L. MONOCYTOGENES* | 8 | 7000 | 3B | 2.13 | 1 |
| *L. MONOCYTOGENES* | 8 | 6846 | 3B | 2.24 | 1 |
| *L. MONOCYTOGENES* | 8 | 6844 | 3B | 2.26 | 1 |
| *L. MONOCYTOGENES* | 8 | 6996 | 1/2A | 1.99 | 1 |
| *L. MONOCYTOGENES* | 8 | 6994 | 1/2A | 2.20 | 1 |
| *L. MONOCYTOGENES* | 8 | 6990 | 3A | 2.10 | 1 |
| *L. MONOCYTOGENES* | 8 | 6840 | 4C | 1.93 | 1 |
| *L. MONOCYTOGENES* | 8 | 6838 | 4B | 1.93 | 1 |
| *L. MONOCYTOGENES* | 8 | 6995 | 1/2A | 2.27 | 1 |
| *L. MONOCYTOGENES* | 8 | 6836 | 4D | 1.51 | 1 |
| *L. MONOCYTOGENES* | 8 | 6989 | 1/2B | 2.12 | 1 |
| *L. MONOCYTOGENES* | 8 | 6853 | 3B | 1.86 | 1 |
| *L. MONOCYTOGENES* | 8 | 3754 | 4D | 2.26 | 1 |
| *L. MONOCYTOGENES* | 2 | F8935 | 1/2A | 1.88 | 1 |
| *L. MONOCYTOGENES* | 8 | 7008 | 1/2A | 2.27 | 1 |
| *L. MONOCYTOGENES* | 8 | 6988 | 1/2A | 2.28 | 1 |
| *L. MONOCYTOGENES* | 8 | 7009 | 1/2B | 1.84 | 1 |
| *L. MONOCYTOGENES* | 8 | 6855 | 4B | 2.00 | 1 |
| *L. MONOCYTOGENES* | 8 | 6857 | 1/2C | 1.92 | 1 |
| *L. MONOCYTOGENES* | 8 | 7010 | 1/2B | 2.03 | 1 |
| *L. MONOCYTOGENES* | 8 | 6856 | 1/2C | 2.25 | 1 |
| *L. MONOCYTOGENES* | 8 | 7012 | 4B | 1.91 | 1 |
| *L. MONOCYTOGENES* | 8 | 7011 | 1/2B | 2.02 | 1 |
| *L. MONOCYTOGENES* | 8 | 6854 | 3B | 2.25 | 1 |
| *L. MONOCYTOGENES* | 8 | 7007 | 1/2A | 1.93 | 1 |
| *L. MONOCYTOGENES* | 8 | 7015 | 48 | 1.95 | 1 |
| *L. MONOCYTOGENES* | 8 | 7031A | 1/2A | 2.13 | 1 |
| *L. MONOCYTOGENES* | 8 | 7019 | 1/2A | 2.27 | 1 |
| *L. MONOCYTOGENES* | 8 | 6834 | 4B | 1.98 | 1 |
| *L. MONOCYTOGENES* | 8 | 7020 | 1/2A | 2.01 | 1 |
| *L. MONOCYTOGENES* | 8 | 7083 | 4A/B | 2.07 | 1 |
| *L. MONOCYTOGENES* | 8 | 6841 | 4B | 2.07 | 1 |
| *L. MONOCYTOGENES* | 8 | 6843 | 4B | 0.98 | 1 |
| *L. MONOCYTOGENES* | 8 | 7069 | 4A/B | 1.75 | 1 |

TABLE 1-continued

LISTERIA INCLUSIVITY STUDY

| ORGANISM | SOURCE | I.D. NUMBER | SERO TYPE | O.D. 450 nm | HYB+ |
|---|---|---|---|---|---|
| *L. MONOCYTOGENES* | 8 | 7018 | 1/2B | 2.02 | 1 |
| *L. MONOCYTOGENES* | 8 | 7001 | 4B | 1.65 | 1 |
| *L. MONOCYTOGENES* | 8 | 47 | 4A | 1.32 | 1 |
| *L. MONOCYTOGENES* | 8 | 7065 | 4A/B | 1.40 | 1 |
| *L. MONOCYTOGENES* | 8 | 7114 | 3A | 1.87 | 1 |
| *L. MONOCYTOGENES* | 8 | 46 | 4B | 1.40 | 1 |
| *L. MONOCYTOGENES* | 8 | 49 | 4A | 0.86 | 1 |
| *L. MONOCYTOGENES* | 8 | 7032 | 1/2B | 2.15 | 1 |
| *L. MONOCYTOGENES* | 3 | 81-861 | 4B | 1.87 | 1 |
| *L. MONOCYTOGENES* | 2 | F2380 | 4B | 2.17 | 1 |
| *L. MONOCYTOGENES* | 2 | F2392 | 4B | 1.61 | 1 |
| *L. MONOCYTOGENES* | 2 | F7288 | 3A | 2.18 | 1 |
| *L. MONOCYTOGENES* | 1, 2 | 43248, KC1778-HIB | | 2.28 | 1 |
| *L. MONOCYTOGENES* | 1, 2 | 15313, KC1775 | | 1.98 | 1 |
| *L. MONOCYTOGENES* | 2 | F2381 | | 1.86 | 1 |
| *L. MONOCYTOGENES* | 2 | F8870 | 4B | 2.04 | 1 |
| *L. MONOCYTOGENES* | 6 | 592 | | 2.12 | 1 |
| *L. MONOCYTOGENES* | 6 | 510 | | 2.19 | 1 |
| *L. MONOCYTOGENES* | 6 | 464 | | 2.14 | 1 |
| *L. MONOCYTOGENES* | 6 | 474 | 1/2A | 1.91 | 1 |
| *L. MONOCYTOGENES* | 4 | BA5 | 1 | 1.99 | 1 |
| *L. MONOCYTOGENES* | 4 | BA34 | | 2.28 | 1 |
| *L. MONOCYTOGENES* | 4 | BA23 | 1A | 2.27 | 1 |
| *L. MONOCYTOGENES* | 4 | SE35 | 3B | 2.30 | 1 |
| *L. MONOCYTOGENES* | 4 | Brie 231 | 4B | 2.17 | 1 |
| *L. MONOCYTOGENES* | 4 | Brie 18 | 1A | 1.78 | 1 |
| *L. MONOCYTOGENES* | 4 | MC145 | 4B | 2.20 | 1 |
| *L. MONOCYTOGENES* | 4 | Scott A | 4B | 2.09 | 1 |
| *L. MONOCYTOGENES* | 4 | BA-7 | 4 | 2.30 | 1 |
| *L. MONOCYTOGENES* | 4 | SF14 | | 2.30 | 1 |
| *L. MONOCYTOGENES* | 4 | DA5 | 1A | 2.06 | 1 |
| *L. MONOCYTOGENES* | 4 | DA-3 | 4 | 2.19 | 1 |
| *L. MONOCYTOGENES* | 4 | V7 | 1A | 1.98 | 1 |
| *L. MONOCYTOGENES* | 9 | 2662F | | 1.67 | 1 |
| *L. MONOCYTOGENES* | 9 | Cattle Lavoie | | 1.81 | 1 |
| *L. MONOCYTOGENES* | 9 | OA-20 | 4 | 1.17 | 1 |
| *L. MONOCYTOGENES* | 9 | 321LR | | 1.31 | 1 |
| *L. MONOCYTOGENES* | 9 | 266RF | | 1.48 | 1 |
| *L. MONOCYTOGENES* | 9 | 88LR | | 1.31 | 1 |
| *L. MONOCYTOGENES* | 9 | 031852-14 | | 1.92 | 1 |
| *L. MONOCYTOGENES* | 8 | 6847 | 3B | 1.91 | 1 |
| *L. MONOCYTOGENTS* | 8 | 6839 | 4B | 1.86 | 1 |
| *L. MONOCYTOGENES* | 8 | 6827 | 4C | 1.48 | 1 |
| *L. MONOCYTOGENES* | 9 | ORF Ferrisburg | | 1.41 | 1 |
| *L. MONOCYTOGENES* | 9 | Silage-2 | | 1.82 | 1 |
| *L. MONOCYTOGENES* | 9 | 675-2634CA | 1A | 1.77 | 1 |
| *L. MONOCYTOGENES* | 9 | 39RF | | 2.09 | 1 |
| *L. MONOCYTOGENES* | 9 | 675-3CA | 1A | 1.19 | 1 |
| *L. MONOCYTOGENES* | 9 | 4841-KO | 4 | 1.73 | 1 |
| *L. MONOCYTOGENES* | 9 | 675-14CA | 1A | 0.46 | 1 |
| *L. MONOCYTOGENES* | 9 | 675-14CA | 1A | 1.96 | 1 |
| *L. MONOCYTOGENES* | 9 | Silage 4 | | 1.85 | 1 |
| *L. MONOCYTOGENES* | 9 | 035240-19 | | 2.02 | 1 |
| *L. MONOCYTOGENES* | 9 | Murray B | 4B | 1.84 | 1 |
| *L. MONOCYTOGENES* | 9 | 675-9-16CA | 1A | 1.61 | 1 |
| *L. MONOCYTOGENES* | 9 | 62RR | | 2.03 | 1 |
| *L. MONOCYTOGENES* | 9 | 675-1CA | 1A | 1.67 | 1 |
| *L. MONOCYTOGENES* | 9 | Bulk Tank | | 1.22 | 1 |
| *L. MONOCYTOGENES* | 9 | 675-31A | | 1.96 | 1 |
| *L. MONOCYTOGENES* | 9 | 33LF | | 1.73 | 1 |
| *L. MONOCYTOGENES* | 9 | 271RF | | 1.96 | 1 |
| *L. MONOCYTOGENES* | 9 | 50F | | 2.10 | 1 |
| *L. MONOCYTOGENES* | 9 | Harvester isolate | | 1.70 | 1 |
| *L. MONOCYTOGENES* | 9 | F5027 | | 2.06 | 1 |
| *L. MONOCYTOGENES* | 9 | 675-37CA | 1A | 1.79 | 1 |
| *L. MONOCYTOGENES* | 9 | 675-15CA | 4 | 1.98 | 1 |
| *L. MONOCYTOGENES* | 9 | 243D | 4 | 1.33 | 1 |
| *L. MONOCYTOGENES* | 9 | 675-16CA | 1A | 1.94 | 1 |
| *L. MONOCYTOGENES* | 9 | Scott A | 4B | 2.15 | 1 |
| *L. MONOCYTOGENES* | 9 | 675-11CA | IA | 2.08 | 1 |
| *L. MONOCYTOGENES* | 9 | 29F | | 2.12 | 1 |
| *L. MONOCYTOGENES* | 9 | 675-17CA | 1A | 2.08 | 1 |
| *L. MONOCYTOGENES* | 9 | 675-030CA | 1A | 2.13 | 1 |
| *L. MONOCYTOGENES* | 9 | OA-1 | 4 | 1.85 | 1 |
| *L. MONOCYTOGENES* | 9 | LA16 | 4 | 1.74 | 1 |
| *L. MONOCYTOGENES* | 9 | Cow Fetus | | 1.44 | 1 |
| *L. MONOCYTOGENES* | 9 | F5069 | 4B | 2.11 | 1 |
| *L. MONOCYTOGENES* | 9 | 33LR | | 2.07 | 1 |
| *L. MONOCYTOGENES* | 9 | Mercier | 4B | 1.91 | 1 |

TABLE 1-continued

LISTERIA INCLUSIVITY STUDY

| ORGANISM | SOURCE | I.D. NUMBER | SERO TYPE | O.D. 450 nm | HYB+ |
|---|---|---|---|---|---|
| *L. MONOCYTOGENES* | 9 | 675-17-25CA | 1A | 2.02 | 1 |
| *L. MONOCYTOGENES* | 9 | 675-2CA | 1A | 1.96 | 1 |
| *L. MONOCYTOGENES* | 9 | 31LF | | 1.39 | 1 |
| *L. MURRAYI* | 7 | CIP76129 | | 0.34 | 1 |
| *L. MURRAYI* | 1 | 25401 | | 1.80 | 1 |
| *L. SEELIGERI* | 7 | CIP150100 | | 2.28 | 1 |
| *L. SEELIGERI* | 2 | F7891 | | 1.65 | 1 |
| *L. SEELIGERI* | 8 | 3978 | | 1.20 | 1 |
| *L. SEELIGERI* | 8 | 6598 | 68 | 1.46 | 1 |
| *L. SEELIGERI* | 8 | 6745 | 4AB | 1.39 | 1 |
| *L. SEELIGERI* | 8 | 6100 | 1/2B | 2.27 | 1 |
| *L. SEELIGERI* | 8 | 6206 | 6B | 2.11 | 1 |
| *L. SEELIGERI* | 8 | 6345 | 1/2A | 2.28 | 1 |
| *L. SEELIGERI* | 8 | 6101 | 1/2B | 2.19 | 1 |
| *L. SEELIGERI* | 8 | 6735 | 4A | 2.28 | 1 |
| *L. SEELIGERI* | 8 | 6102 | 1/2B | 2.28 | 1 |
| *L. SEELIGERI* | 8 | 4060 | 1/2B | 2.16 | 1 |
| *L. SEELIGERI* | 8 | 3663 | 1/2B | 2.28 | 1 |
| *L. SEELIGERI* | 8 | 3525 | 1/2A | 2.25 | 1 |
| *L. SEELIGERI* | 8 | 3515 | 1/2A | 2.07 | 1 |
| *L. SEELIGERI* | 8 | 3479 | 1/2B | 2.20 | 1 |
| *L. SEELIGERI* | 8 | 3978 | 1/2B | 1.20 | 1 |
| *L. SEELIGERI* | 8 | 6725 | 4A | 2.20 | 1 |
| *L. SEELIGERI* | 2 | KC1785 | | 2.17 | 1 |
| *L. SEELIGERI* | 2 | F7334 | | 2.34 | 1 |
| *L. SEELIGERI* | 4 | Brie 34 | 1 | 1.93 | 1 |
| *L. SEELIGERI* | 4 | DA41 | | 2.24 | 1 |
| *L. SEELIGERI* | 4 | MC142 | | 2.15 | 1 |
| *L. SEELIGERI* | 4 | AT2 | | 2.20 | 1 |
| *L. SEELIGERI* | 4 | LA15 | 1 | 2.11 | 1 |
| *L. SPP* | 11 | AJ5520 | | 2.03 | 1 |
| *L. SPP* | 11 | 3620 | | 2.01 | 1 |
| *L. WELSHIMERI* | 7 | CIP8169 | | 1.39 | 1 |
| *L. WELSHIMERI* | 2 | F8918 | | 1.79 | 1 |
| *L. WELSHIMERI* | 2, 8 | 5332, KC1825 | 1/2A | 2.26 | 1 |
| *L. WELSHIMERI* | 8 | 5828 | 6A | 1.41 | 1 |
| *L. WELSHIMERI* | 8 | 5333 | 6B | 1.97 | 1 |
| *L. WELSHIMERI* | 8 | 5825 | 6A | 0.92 | 1 |
| *L. WELSHIMERI* | 8 | 6199 | 6A | 2.22 | 1 |
| *L. WELSHIMERI* | 8 | 5332 | | 2.01 | 1 |
| *L. WELSHIMERI* | 8 | 3809 | 6A | 2.25 | 1 |
| *L. WELSHIMERI* | 3 | RM177 | | 2.22 | 1 |
| *L. WELSHIMERI* | 3 | RM213 | | 2.17 | 1 |
| *L. WELSHIMERI* | 2, 8 | 5333, KC1826 | 6B | 2.22 | 1 |
| *L. WELSHIMERI* | 2, 8 | 5877, KC1828 | | 2.33 | 1 |
| *L. WELSHIMERI* | 1, 2 | ATCC35897, KC1836 | | 2.17 | 1 |
| *L. WELSHIMERI* | 4 | 24-34KA | 4 | 0.43 | 1 |
| *L. WELSHIMERI* | 4 | 4889A | | 2.24 | 1 |
| *L. WELSHIMERI* | 4 | 2436A | 4 | 1.39 | 1 |

SOURCE KEY:
1 AMERICAN TYPE CULTURE COLLECTION ROCKVILLE, MD
2 CENTERS FOR DISEASE CONTROL ATLANTA, GA
3 BUREAU OF MICROBIAL HAZARDS HEALTH PROTECTION BRANCH OTTOWA, CANADA
4 U.S. FOOD AND DRUG ADMINISTRATION CINCINNAT, OH
5 GENE-TRAK SYSTEMS FRAMINGHAM, MA
6 MASSACHUSETTS DEPARTMENT OF HEALTH JAMAICA PLAINS, MA
7 PASTEUR INSTITUTE PARIS, FRANCE
8 SIELIKER LABORATORIES CHICAGO HEIGHTS, IL
9 UNIVERSITY OF VERMONT BURLINGTON, VT
10 U.S. DEPARTMENT OF AGRICULTURE BELTSVILLE, MD
11 YALE UNIVERSITY NEW HAVEN, CT

TABLE 2

LISTERIA EXCLUSIVITY STUDY

| ORGANISM | SOURCE | I.D. NUMBER | O.D. 450 nm | HYB+ |
|---|---|---|---|---|
| *ACINETOBACTER CALCOACETIUS* | 1 | ATCC 19605 | <0.1 | 0 |
| *AEROMONAS HYDROPHILIA* | 1 | ATCC 7965 | <0.1 | 0 |
| *BACILLUS BREVIS* | 1 | ATCC 8186 | <0.1 | 0 |
| *BACILLUS CEREUS* | 1 | ATCC 14579 | <0.1 | 0 |
| *BACILLUS COAGULUS* | 1 | ATCC 7050 | <0.1 | 0 |
| *BACILLUS SUBTILTS* | 1 | ATCC 6051 | <0.1 | 0 |
| *BROCHOTHRIX THERMOSPHACTA* | 1 | ATCC 11509 | <0.1 | 0 |
| *CITROBACTER DIVERSUS* | 1 | ATCC 27156 | <0.1 | 0 |
| *CITROBACTER FREUNDII* | 8 | S118A | <0.1 | 0 |
| *CITROBACTER FREUNDII* | 8 | S135 | <0.1 | 0 |
| *CLOSTRIDIUM BIFERMENTANS* | 1 | ATCC 638 | <0.1 | 0 |

TABLE 2-continued

LISTERIA EXCLUSIVITY STUDY

| ORGANISM | SOURCE | I.D. NUMBER | O.D. 450 nm | HYB+ |
|---|---|---|---|---|
| *CLOSTRIDIUM DIFFICILE* | 1 | ATCC 9689 | <0.1 | 0 |
| *CLOSTRIDIUM PERFRINGENS* | 1 | ATCC 3264 | <0.1 | 0 |
| *CLOSTRIDIUM SORDELLII* | 1 | ATCC 9714 | <0.1 | 0 |
| *CORYNEBACTERIUM GENITALIUM* | 1 | ATCC 33031 | <0.1 | 0 |
| *CORYNEBACTERIUM XEROSIS* | 1 | ATCC 373 | <0.1 | 0 |
| *ENTEROBACTER AEROGENES* | 1 | ATCC 13048 | <0.1 | 0 |
| *ENTEROBACTER AGGLOMERANS* | 8 | S121B | <0.1 | 0 |
| *ENTEROBACTER CLOACAE* | 8 | S135 | <0.1 | 0 |
| *ENTEROCOCCUS HIRAE* | 1 | ATCC 35220 | <0.1 | 0 |
| *ESCHERICHIA COLI* | 1 | ATCC 12035 | <0.1 | 0 |
| *HAFNIA ALVEI* | 1 | ATCC 29927 | <0.1 | 0 |
| *KLEBSIELLA OXYTOCA* | 1 | ATCC 13182 | <0.1 | 0 |
| *KLEBSIELLA PNEUMONIAE* | 8 | S122F | <0.1 | 0 |
| *KURTHIA ZOPFII* | 1 | ATCC 33403 | <0.1 | 0 |
| *JONESIA DENITRIFICANS* | 5 | GT 0666 | <0.1 | 0 |
| *LACTOBACILLUS ACIDOPHILUS* | 1 | ATCC 4356 | <0.1 | 0 |
| *LACTOBACILLUS MINUTUS* | 1 | ATCC 33267 | <0.1 | 0 |
| *LACTOBACILLUS PLANTARUM* | 1 | ATCC 8014 | <0.1 | 0 |
| *MICROCOCCUS SPECIES* | 5 | GT 0298 | <0.1 | 0 |
| *MICROCOCCUS SPECIES* | 5 | GT 0299 | <0.1 | 0 |
| *MORGANELLA MORGANII* | 1 | ATCC 25830 | <0.1 | 0 |
| *PROTEUS MIRABILIS* | 5 | GT 0364 | <0.1 | 0 |
| *PROTEUS VULGARIS* | 1 | ATCC 29905 | <0.1 | 0 |
| *PROTEUS VULGARIS* | 8 | S133 | <0.1 | 0 |
| *PROVIDENCIA RETTIGERI* | 1 | ATCC 29944 | <0.1 | 0 |
| *PROVIDENCIA STUARTII* | 1 | ATCC 29914 | <0.1 | 0 |
| *PSEUDOMONAS ACIDOVORANS* | 1 | ATCC 15668 | <0.1 | 0 |
| *PSEUDOMONAS AERUGINOSA* | 5 | IG 928 | <0.1 | 0 |
| *PSEUDOMONAS PAUCOMOBILIS* | 5 | GT 0379 | <0.1 | 0 |
| *RHODOCOCCUS EQUI* | 1 | ATCC 6939 | <0.1 | 0 |
| *SALMONELLA ANATUM* | 2 | 715-82 | <0.1 | 0 |
| *SALMONELLA BLEDGAM* | 2 | STK68 | <0.1 | 0 |
| *SALMONELLA TYPHIMURIUM* | 1 | ATCC 23566 | <0.1 | 0 |
| *SERRATIA MARCESENS* | 1 | ATCC 29937 | <0.1 | 0 |
| *SHIGELLA SONNEII* | 2 | STK814 | <0.1 | 0 |
| *STAPHYLOCOCCUS AUREUS* | 1 | ATCC 12600 | <0.1 | 0 |
| *STAPHYLOCOCCUS AUREUS* | 5 | GT 0400 | <0.1 | 0 |
| *STAPHYLOCOCCUS EPIDERMIDIS* | 5 | GT 0402 | <0.1 | 0 |
| *STAPHYLOCOCCUS EPIDERMIDIS* | 5 | GT 0403 | <0.1 | 0 |
| *STAPHYLOCOCCUS EPIDERMIDIS* | 1 | ATCC 14990 | <0.1 | 0 |
| *STAPHYLOCOCCUS HOMINIS* | 1 | ATCC 27844 | <0.1 | 0 |
| *STAPHYLOCOCCUS SAPROPHYTICUS* | 1 | ATCC 15305 | <0.1 | 0 |
| *STREPTOCOCCUS AGALACTICAE* | 1 | ATCC 13813 | <0.1 | 0 |
| *STREPTOCOCCUS BOVIS* | 1 | ATCC 15351 | <0.1 | 0 |
| *STREPTOCOCCUS FAECIUM* | 1 | ATCC 6056 | <0.1 | 0 |
| *STREPTOCOCCUS FECALIS* | 1 | ATCC 19433 | <0.1 | 0 |
| *STREPTOCOCCUS GALLINARUM* | 1 | ATCC 35038 | <0.1 | 0 |
| *STREPTOCOCCUS LACTIS* | 1 | ATCC 11454 | <0.1 | 0 |
| *STREPTOCOCCUS MUTANS* | 1 | ATCC 25175 | <0.1 | 0 |
| *STREPTOCOCCUS PNEUMONIAE* | 1 | ATCC 6303 | <0.1 | 0 |
| *STREPTOCOCCUS PYOGENES* | 1 | ATCC 19615 | <0.1 | 0 |
| *STREPTOCOCCUS SALIVARUS* | 1 | ATCC 13419 | <0.1 | 0 |
| *STREPTOCOCCUS BANGUIS* | 1 | ATCC 10556 | <0.1 | 0 |
| *YERSINIA ENTEROCOLITICA* | 1 | ATCC 9610 | <0.1 | 0 |

SOURCE KEY:
1 AMERICAN TYPE CULTURE COLLECTION ROCKVILLE, MD
2 CENTERS FOR DISEASE CONTROL ATLANTA, GA
5 GENE-TRAK SYSTEMS FRAMINGHAM, MA
8 SIELIKER LABORATORIES CHICAGO HEIGHTS, IL

TABLE 3

FOOD STUDY

| SAMPLE | STRAIN | CELLS/ SAMPLE | O.D. 450 nm | ASSAY RESULT | MICRO CONFIRM |
|---|---|---|---|---|---|
| Total | | | | 51 | 51 |
| Raw Shrimp | *Listeria monocytogenes* | 114 | 1.84 | 1 | 1 |
| Raw Shrimp | *Listeria monocytogenes* | 11 | 0.06 | 0 | 0 |
| Raw Shrimp | control | | 0.07 | 0 | 0 |
| Raw Shrimp | *Listeria monocytogenes* | 120 | 1.39 | 1 | 1 |
| Raw Shrimp | *Listeria monocytogenes* | 12 | 0.05 | 0 | 0 |
| Raw Shrimp | control | | 0.06 | 0 | 0 |
| Raw Shrimp | *Listeria innocua* | 78 | 0.75 | 1 | 1 |
| Raw Shrimp | *Listeria innocua* | 8 | 0.04 | 0 | 0 |
| Raw Shrimp | control | | 0.04 | 0 | 0 |
| Raw Shrimp | *Listeria ivanovii* | 58 | 0.14 | 1 | 1 |
| Raw Shrimp | *Listeria ivanovii* | 6 | 0.15 | 1 | 1 |

TABLE 3-continued

| | | FOOD STUDY | | | |
|---|---|---|---|---|---|
| SAMPLE | STRAIN | CELLS/ SAMPLE | O.D. 450 nm | ASSAY RESULT | MICRO CONFIRM |
| Raw Shrimp | control | | 0.05 | 0 | 0 |
| Crabmeat | *Listeria monocytogenes* | 114 | 1.92 | 1 | 1 |
| Crabmeat | *Listeria monocytogenes* | 11 | 0.02 | 0 | 0 |
| Crabmeat | control | | 0.04 | 0 | 0 |
| Crabmeat | *Listeria monocytogenes* | 120 | 1.88 | 1 | 1 |
| Crabmeat | *Listeria monocytogenes* | 12 | 0.05 | 0 | 0 |
| Crabmeat | control | | 0.04 | 0 | 0 |
| Crabmeat | *Listeria innocua* | 76 | 1.87 | 1 | 1 |
| Crabmeat | *Listeria innocua* | 8 | 1.87 | 1 | 1 |
| Crabmeat | control | | 0.04 | 0 | 0 |
| Crabmeat | *Listeria ivanovii* | 58 | 1.87 | 1 | 1 |
| Crabmeat | *LIsteria ivanovii* | 6 | 0.04 | 0 | 0 |
| Crabmeat | control | | 0.05 | 0 | 0 |
| Chicken pie | *Listeria monocytogenes* | 114 | 1.88 | 1 | 1 |
| Chicken pie | *Listeria monocytogenes* | 11 | 1.84 | 1 | 1 |
| Chicken pie | control | | 0.03 | 0 | 0 |
| Chicken pie | *Listeria monocytogenes* | 120 | 1.87 | 1 | 1 |
| Chicken pie | *Listeria monocytogenes* | 12 | 1.88 | 1 | 1 |
| Chicken pie | control | | 0.03 | 0 | 0 |
| Chicken pie | *Listeria innocua* | 76 | 1.87 | 1 | 1 |
| Chicken pie | *Listeria innocua* | 8 | 0.00 | 0 | 0 |
| Chicken pie | control | | 0.03 | 0 | 0 |
| Chicken pie | *Listeria ivanovii* | 58 | 1.77 | 1 | 1 |
| Chicken pie | *Listeria ivanovii* | 6 | 1.85 | 1 | 1 |
| Chicken pie | control | | 0.03 | 0 | 0 |
| Beef franks | *Listeria monocytogenes* | 114 | 1.91 | 1 | 1 |
| Beef franks | *Listeria monocytogenes* | 11 | 0.03 | 0 | 0 |
| Beef franks | control | | 1.77 | 1 | 1 |
| Beef franks | *Listeria monocytogenes* | 120 | 1.88 | 1 | 1 |
| Beef franks | *Listeria monocytogenes* | 12 | 0.04 | 0 | 0 |
| Beef franks | control | | 0.04 | 0 | 0 |
| Beef-franks | *Listeria innocua* | 76 | 1.85 | 1 | 1 |
| Beef franks | *Listeria innocua* | 8 | 1.90 | 1 | 1 |
| Beef franks | control | | 0.02 | 0 | 0 |
| Beef franks | *Listeria ivanovii* | 58 | 1.87 | 1 | 1 |
| Beef franks | *Listeria ivanovii* | 6 | 1.79 | 1 | 1 |
| Beef franks | control | | 0.00 | 0 | 0 |
| Salami | *Listeria monocytogenes* | 114 | 1.86 | 1 | 1 |
| Salami | *Listeria monocytogenes* | 11 | 0.00 | 0 | 0 |
| Salami | control | | 0.01 | 0 | 0 |
| Salami | *Listeria monocytogenes* | 120 | 1.74 | 1 | 1 |
| Salami | *Listeria monocytogenes* | 12 | 0.01 | 0 | 0 |
| Salami | control | | 0.12 | 0 | 0 |
| Salami | *Listeria innocua* | 76 | 1.86 | 1 | 1 |
| Salami | *Listeria innocua* | 8 | 1.62 | 1 | 1 |
| Salami | control | | 0.06 | 0 | 0 |
| Salami | *Listeria ivanovii* | 58 | 1.64 | 1 | 1 |
| Salami | *Listeria ivanovii* | 6 | 1.76 | 1 | 1 |
| Salami | control | | 0.05 | 0 | 0 |
| Ground turkey | *Listeria monocytogenes* | 114 | 1.79 | 1 | 1 |
| Ground turkey | *Listeria monocytogenes* | 11 | 1.79 | 1 | 1 |
| Ground turkey | control | | 0.05 | 0 | 0 |
| Ground turkey | *Listeria monocytogenes* | 120 | 1.75 | 1 | 1 |
| Ground turkey | *Listeria monocytogenes* | 12 | 1.69 | 1 | 1 |
| Ground turkey | control | | 0.05 | 0 | 0 |
| Ground turkey | *Listeria innocua* | 76 | 1.49 | 1 | 1 |
| Ground turkey | *Listeria innocua* | 8 | 0.06 | 0 | 0 |
| Ground turkey | control | | 0.03 | 0 | 0 |
| Ground turkey | *Listeria ivanovii* | 58 | 1.73 | 1 | 1. |
| Ground turkey | *Listeria ivanovii* | 6 | 1.71 | 1 | 1 |
| Ground turkey | control | | 1.65 | 1 | 1 |
| Surimi | *Listeria monocytogenes* | 114 | 1.59 | 1 | 1 |
| Surimi | *Listeria monocytogenes* | 11 | 1.68 | 1 | 1 |
| Surimi | control | | 0.04 | 0 | 0 |
| Surimi | *Listeria monocytogenes* | 120 | 1.73 | 1 | 1 |
| Surimi | *Listeria monocytogenes* | 12 | 1.71 | 1 | 1 |
| Surimi | control | | 0.05 | 0 | 0 |
| Surimi | *Listeria innocua* | 76 | 1.64 | 1 | 1 |
| Surimi | *Listeria innocua* | 8 | 1.61 | 1 | 1 |
| Surimi | control | | 0.06 | 0 | 0 |
| Surimi | *Listeria ivanovii* | 58 | 1.64 | 1 | 1 |
| Surimi | *Listeria ivanovii* | 6 | 0.03 | 0 | 0 |
| Surimi | control | | 0.03 | 0 | 0 |
| Cabbage | *Listeria monocytogenes* | 114 | 0.99 | 1 | 1 |
| Cabbage | *Listeria monocytogenes* | 11 | 0.05 | 0 | 0 |
| Cabbage | control | | 0.05 | 0 | 0 |
| Cabbage | *Listeria mohocytogenes* | 120 | 1.77 | 1 | 1 |
| Cabbage | *Listeria monocytogenes* | 12 | 0.04 | 0 | 0 |
| Cabbage | control | | 0.06 | 0 | 0 |

TABLE 3-continued

| | | FOOD STUDY | | | |
|---|---|---|---|---|---|
| SAMPLE | STRAIN | CELLS/ SAMPLE | O.D. 450 nm | ASSAY RESULT | MICRO CONFIRM |
| Cabbage | *Listeria innocua* | 76 | 1.74 | 1 | 1 |
| Cabbage | *Listeria innocua* | 8 | 1.66 | 1 | 1 |
| Cabbage | control | | 0.03 | 0 | 0 |
| Cabbage | *Listeria ivanovii* | 58 | 1.63 | 1 | 1 |
| Cabbage | *Listeria ivanovii* | 6 | 1.44 | 1 | 1 |
| Cabbage | control | | 0.03 | 0 | 0 |

Assay Cut off = 0.12

What is claimed is:

1. An isolated nucleic acid probe consisting of a nucleotide sequence at least 10 and less than 134 nucleotides in length within the region 406 to 538 of the 16S rRNA of *Listeria monocytogenes* or a nucleotide sequence fully complementary to said nucleotide sequence, which nucleic acid probe preferentially hybridizes to the rRNA or rDNA of Listeria over rRNA or rDNA of non-Listeria bacteria.

2. The nucleic acid probe of claim 1 wherein said non-Listeria bacteria comprise *Acinetobacter calcoacetius, Aeromonas hydrophilia, Bacillus brevis, Bacillus cereus, Bacillus coagulans, Bacillus subtilis, Brochothrix thermosphacta, Citrobacter diversus, Citrobacter freundii, Clostridium bifermentans, Clostridium difficile, Clostridium perfringens, Clostridium sordellii, Corynebacterium genitalium, Corynebacterium xerosis, Enterobacter aerogenes, Enterobacter agglomerans, Enterobacter cloacae, Enterococcus hirae, Escherichia coli, Hafnia alvei, Klebsiella oxytoca, Klebsiella pneumoniae, Kurthia zopfii, Jonesia denitrificans, Lactobacillus acidophilus, Lactobacillus minutus, Lactobacillus plantarum, Morganella morganii, Proteus mirabilis, Proteus vulgaris, Providencia rettigeri, Providencia situartii, Pseudomonas acidovorans, Pseudomonas aeruginosa, Pseudomonas paucomobilis, Rhocococcus equii, Salmonella anatum, Salmonella bledgam, Salmonella typhimurium, Serratia marcescens, Shigella sonnei, Staphylococcus aureus, Staphylococcus epidermidis, Staphylococcus hominis, Staphylococcus saprophyticus, Streptococcus agalacticae, Streptococcus bovis, Streptococcus faecium, Streptococcus faecalis, Streptococcus gallinarum, Streptococcus lactis, Streptococcus mutants, Streptococcus pneumoniae, Streptococcus pyogenes, Streptococcus salivarus, Streptococcus sanguis and Yersinia enterocolitica.*

3. A set of nucleic acid probes comprising at least a first nucleic acid probe consisting of a first nucleotide sequence at least 10 and less than 134 nucleotides in length within the region 448 to 492 of the 16S rRNA of *Listeria monocytogenes* or a nucleotide sequence fully complementary to said first nucleotide sequence which first nucleic acid probe preferentially hybridizes to the rRNA or rDNA of Listeria over rRNA or rDNA of non-Listeria bacteria and a second nucleic acid probe consisting of a second nucleotide sequence at least 10 and less than 134 nucleotides in length within the region 406 to 447 or region 493 to 538 of the 16S rRNA of *Listeria monocytogenes* or a nucleotide sequence fully complementary to said second nucleotide sequence.

4. The set of nucleic acid probes of claim 2, wherein said nucleic acid probe set is selected from the group of probe sets consisting of probes 1120 and 1119; 1212 and 1118; 1120 and 1212; 1120 and 1118; a nucleotide sequence fully complementary to probe 1120 and a nucleotide sequence fully complementary to probe 1119; a nucleotide sequence fully complementary to probe 1212 and a nucleotide sequence fully complementary to probe 1118; a nucleotide sequence fully complementary to probe 1120 and a nucleotide sequence fully complementary to probe 1212; or a nucleotide sequence fully complementary to 1120 and a nucleotide sequence fully complementary to probe 1118.

5. A method for detecting the presence of Listeria in a sample comprising:

a) containing said sample with a nucleic acid probe of claim 1;

b) imposing hybridization conditions on said sample and the nucleic acid probe to allow the nucleic acid probe to hybridize to the rRNA or rDNA of Listeria, if present in said sample, to form hybridized nucleic acid complexes, under conditions which do not allow said nucleic acid probe to form stable hybridized nucleic acid complexes with non-Listeria bacteria rRNA or rDNA; and c) detecting said hybridized nucleic acid complexes as an indication of the presence of said Listeria in said sample.

6. The method of claim 5 wherein said contacting is with a nucleic acid probe set selected from the group of probe sets consisting of probes 1120 and 1119; 1212 and 1118; 1120 and 1212; 1120 and 1118; a nucleotide sequence fully complementary to probe 1120 and a nucleotide sequence fully complementary to probe 1119; a nucleotide sequence fully complementary to probe 1212 and a nucleotide sequence fully complementary to probe 1118; a nucleotide sequence fully complementary to probe 1120 and a nucleotide sequence fully complementary to probe 1212; or a nucleotide sequence fully complementary to probe 1120 and a nucleotide sequence fully complementary to probe 1118.

7. An assay kit for detecting Listeria comprising the nucleic acid probe of claim 1, hybridization buffer and container.

8. An assay kit for detecting Listeria comprising a set of at least two nucleic acid probes as defined in claim 3, hybrization buffer and a container.

9. The assay kit of claim 8, wherein said nucleic acid probe set is selected from the group of probe sets consisting of probes 1120 and 1119; 1212 and 1118; 1120 and 1212; and 1120 and 1118; a nucleotide sequence fully complementary to probe 1120 and a nucleotide sequence complementary to probe 1119; a nucleotide sequence fully complementary to probe 1212 and a nucleotide sequence fully complementary to probe 1118; a nucleotide sequence fully complementary to probe 1120 and a nucleotide sequence fully complementary to probe 1212; or a nucleotide sequence fully complementary to probe 1120 and a nucleotide sequence fully complementary to 1118.

10. A probe of claim 1 wherein said nucleotide sequence consists of the nucleotide sequence of probe

1120, or a nucleotide sequence fully complementary to the nucleotide sequence of probe 1120.

11. A probe of claim 1 wherein said nucleotide sequence consists of the nucleotide sequence of probe 1119, or a nucleotide sequence fully complementary to the nucleotide sequence of probe 1119.

12. A probe of claim 1 wherein said nucleotide sequence consists of the nucleotide sequence of probe 1212, or a nucleotide sequence fully complementary to the nucleotide sequence of probe 1212.

13. A probe of claim 1 wherein said nucleotide sequence consists of the nucleotide sequence of probe 1118, or a nucleotide sequence fully complementary to the nucleotide sequence of probe 1118.

* * * * *

UNITED STATES PATENT AND TRADEMARK OFFICE

CERTIFICATE OF CORRECTION

PATENT NO. : 5,376,528

DATED : December 27, 1994

INVENTOR(S) : Walter King, Jyotsna S. Shah, Raymond M. Nietupski, Susan Raposa, Jane Warshaw, Patrick Groody, Jonathan Lawrie, George Parsons, Donald N. Halbert and David J. Lane It is certified that error appears in the above-identified patent and that said Letters Patent is hereby corrected as shown below:

Title page, [75] Inventors: after Jonathan Lawrie, please delete "Milford, Mass." and insert therefor --Cary, N.C.--.

Cover page, [56] References Cited, FOREIGN PATENT DOCUMENTS, at EPO Reference 0314294, delete "of 0000". (This was blank when filed.)

Cover page, [56] References Cited, OTHER PUBLICATIONS, insert the following reference: --Thuong et al., P.N.A.S., USA, 84:5129-5133 (1987)--.

Col. 7, line 23, please delete "shows" and insert therefor --show--.

Col. 12, line 37, please delete "Specifics" and insert therefor --Specific--.

Cols. 15-16, Table 1, line 10, please delete "5541" and insert therefor --6541--.

Cols. 15-16, Table 1, line 13, please delete "a" and insert therefor --8--.

UNITED STATES PATENT AND TRADEMARK OFFICE

CERTIFICATE OF CORRECTION

PATENT NO. : 5,376,528

DATED : December 27, 1994

INVENTOR(S) : Walter King, Jyotsna S. Shah, Raymond M. Nietupski, Susan Raposa, Jane Warshaw, Patrick Groody, Jonathan Lawrie, George Parsons, Donald N. Halbert and David J. Lane It is certified that error appears in the above-identified patent and that said Letters Patent is hereby corrected as shown below:

Cols. 15-16, Table 1, line 38, please delete "6" and insert therefor --5--.

Cols. 15-16, Table 1, line 40, please delete "a" and insert therefor --8--.

Cols. 15-16, Table 1, line 46, please delete "2.15" and insert therefor --2.16--.

Cols. 15-16, Table 1, line 57, please delete "15-438-143" and insert therefor --15-43B-143--.

Cols. 15-16, Table 1, line 67, please delete "L. MONOCYTOGENE" and insert therefor --L. MONOCYTOGENES--.

Cols. 17-18, Table 1, line 3, please delete "2" and insert therefor --8--.

Cols. 17-18, Table, 1, line 66, please delete "2.25" and insert therefor --2.26--.

Cols. 17-18, Table 1, line 71, please delete "48" and insert therefor --4B--.

Cols. 21-22, Table 1, line 32, please delete "3620" and insert therefor --3520--.

UNITED STATES PATENT AND TRADEMARK OFFICE

CERTIFICATE OF CORRECTION

PATENT NO. : 5,376,528

DATED : December 27, 1994

INVENTOR(S) : Walter King, Jyotsna S. Shah, Raymond M. Nietupski, Susan Raposa, Jane Warshaw, Patrick Groody, Jonathan Lawrie, George Parsons, Donald N. Halbert and David J. Lane It is certified that error appears in the above-identified patent and that said Letters Patent is hereby corrected as shown below:

Cols. 21-22, Table 1, Source Key, please delete "SIELIKER" and insert therefor --SILLIKER--.

Cols. 21-22, Table 2, line 1, please delete "19605" and insert therefor --19606--.

Cols. 21-22, Table 2, line 6, please delete "SUBTILTS" and insert therefor --SUBTILIS--.

Cols. 23-24, Table 2, line 10, please delete "12035" and insert therefor --12036--.

Cols. 23-24, Table 2, line 53, please delete "BANGUIS" and insert therefor --SANGUIS--.

Cols. 23-24, Table 2, Source Key, please delete "SIELIKER" and insert therefor --SILLIKER--.

Cols. 25-26, Table 3, line 12, please delete "Llsteria" and insert therefor --Listeria--.

Cols. 25-26, Table 3, line 32, please delete "Beef-franks" and insert therefor --Beef franks--.

Cols. 25-26, Table 3, line 77, please delete "mohocytogenes" and insert therefor --monocytogenes--.

Col. 27, line 61, please delete "claim 2" and insert therefor --claim 3--.

UNITED STATES PATENT AND TRADEMARK OFFICE
CERTIFICATE OF CORRECTION

PATENT NO. : 5,376,528 Page 4 of 4

DATED : December 27, 1994

INVENTOR(S) : Walter King, Jyotsna S. Shah, Raymond M. Nietupski, Susan Raposa, Jane Warshaw, Patrick Groody, Jonathan Lawrie, George Parsons, Donald N. Halbert and David J. Lane It is certified that error appears in the above-identified patent and that said Letters Patent is hereby corrected as shown below:

Col. 28, line 22, please delete "containing" and insert therefor --contacting--.

Col. 28, line 49, after "and" please insert --a--.

Col. 28, line 53, please delete "hybrization" and insert therefor --hybridization--.

Signed and Sealed this

Eleventh Day of June, 1996

Attest:

BRUCE LEHMAN

Attesting Officer

Commissioner of Patents and Trademarks